(12) United States Patent
Spodsberg

(10) Patent No.: US 9,169,473 B2
(45) Date of Patent: Oct. 27, 2015

(54) POLYPEPTIDES HAVING XYLANASE ACTIVITY AND POLYNUCLEOTIDES ENCODING SAME

(71) Applicants: Novozymes A/S, Bagsvaerd (DK); Novozymes Inc., Davis, CA (US)

(72) Inventor: Nikolaj Spodsberg, Bagsvaerd (DK)

(73) Assignee: Novozymes, Inc., Davis, CA (US)

( * ) Notice: Subject to any disclaimer, the term of this patent is extended or adjusted under 35 U.S.C. 154(b) by 87 days.

(21) Appl. No.: 13/765,267

(22) Filed: Feb. 12, 2013

(65) Prior Publication Data

US 2014/0227761 A1    Aug. 14, 2014

(51) Int. Cl.
*C12N 9/24*    (2006.01)

(52) U.S. Cl.
CPC ....... *C12N 9/2482* (2013.01); *C12Y 302/01008* (2013.01)

(58) Field of Classification Search
None
See application file for complete search history.

(56) References Cited

FOREIGN PATENT DOCUMENTS

WO    WO 2012/092676 A1 *   7/2012

* cited by examiner

*Primary Examiner* — Suzanne M Noakes
(74) *Attorney, Agent, or Firm* — Robert L. Stames

(57) ABSTRACT

The present invention relates to isolated polypeptides having xylanase activity and polynucleotides encoding the polypeptides. The invention also relates to nucleic acid constructs, vectors, and host cells comprising the polynucleotides as well as methods of producing and using the polypeptides.

5 Claims, No Drawings

SEQUENCE LISTING

<160> NUMBER OF SEQ ID NOS: 12

<210> SEQ ID NO 1
<211> LENGTH: 1518
<212> TYPE: DNA
<213> ORGANISM: Trametes versicolor
<220> FEATURE:
<221> NAME/KEY: CDS
<222> LOCATION: (1)..(258)
<220> FEATURE:
<221> NAME/KEY: sig_peptide
<222> LOCATION: (1)..(54)
<220> FEATURE:
<221> NAME/KEY: mat_peptide
<222> LOCATION: (55)..()
<220> FEATURE:
<221> NAME/KEY: Intron
<222> LOCATION: (259)..(319)
<220> FEATURE:
<221> NAME/KEY: CDS
<222> LOCATION: (320)..(410)
<220> FEATURE:
<221> NAME/KEY: Intron
<222> LOCATION: (411)..(464)
<220> FEATURE:
<221> NAME/KEY: CDS
<222> LOCATION: (465)..(591)
<220> FEATURE:
<221> NAME/KEY: Intron
<222> LOCATION: (592)..(645)
<220> FEATURE:
<221> NAME/KEY: CDS
<222> LOCATION: (646)..(651)
<220> FEATURE:
<221> NAME/KEY: Intron
<222> LOCATION: (652)..(701)
<220> FEATURE:
<221> NAME/KEY: CDS
<222> LOCATION: (702)..(715)
<220> FEATURE:
<221> NAME/KEY: Intron
<222> LOCATION: (716)..(778)
<220> FEATURE:
<221> NAME/KEY: CDS
<222> LOCATION: (779)..(925)
<220> FEATURE:
<221> NAME/KEY: Intron
<222> LOCATION: (926)..(978)
<220> FEATURE:
<221> NAME/KEY: CDS
<222> LOCATION: (979)..(1283)
<220> FEATURE:
<221> NAME/KEY: Intron
<222> LOCATION: (1284)..(1345)
<220> FEATURE:
<221> NAME/KEY: CDS
<222> LOCATION: (1346)..(1402)
<220> FEATURE:
<221> NAME/KEY: Intron
<222> LOCATION: (1403)..(1464)
<220> FEATURE:
<221> NAME/KEY: CDS
<222> LOCATION: (1465)..(1515)

<400> SEQUENCE: 1 atg cac ttc tca ctc ctc gca gcc ttc atc gcg ctg gct ccg gcc gcg      48
Met His Phe Ser Leu Leu Ala Ala Phe Ile Ala Leu Ala Pro Ala Ala
            -15                 -10                 -5 ctc gcg atc ccc gcg acc ccc gtg gtc gat gcg agt ctc ccc ggc tcg      96
Leu Ala Ile Pro Ala Thr Pro Val Val Asp Ala Ser Leu Pro Gly Ser
     -1  1                5                  10 acc gcg aac gtg gcg ggt ctg cac gcc gtc gcg aag gcg gcg ggc aag     144
Thr Ala Asn Val Ala Gly Leu His Ala Val Ala Lys Ala Ala Gly Lys
 15                  20                  25                  30

| | |
|---|---|
| ctc tac ttg ggc act gcg acg gac aat aac gag ctt acc aac acg cag<br>Leu Tyr Leu Gly Thr Ala Thr Asp Asn Asn Glu Leu Thr Asn Thr Gln<br>                35                    40                    45 | 192 |
| tac acc gcc atc ctc gag gct ccg aac atg ttc ggc cag atc acc gcc<br>Tyr Thr Ala Ile Leu Glu Ala Pro Asn Met Phe Gly Gln Ile Thr Ala<br>              50                    55                    60 | 240 |
| gag aac acc atg aaa tgg gtcagttgcg ccttgtcgcg atgttccgag<br>Glu Asn Thr Met Lys Trp<br>              65 | 288 |
| cacgttccgc aagctaacga tttgatgcta g gac gcg acc gag ccc cag cag<br>                                            Asp Ala Thr Glu Pro Gln Gln<br>                                                    70                          75 | 340 |
| aac gtg ttc acg ttc acg cag ggc gac cag atc gcg aac ctg gcg aag<br>Asn Val Phe Thr Phe Thr Gln Gly Asp Gln Ile Ala Asn Leu Ala Lys<br>              80                    85                    90 | 388 |
| tcc cac ggg atg ctg ctg cgc g gtaacgacag tcttgaaggg gccgaaaatg<br>Ser His Gly Met Leu Leu Arg<br>                      95 | 440 |
| tggaagaact gaatgttttc gcag gt   cac aac tgc gtc tgg cac caa cag<br>                                   Gly His Asn Cys Val Trp His Gln Gln<br>                                          100                    105 | 490 |
| ctc ccg agc tgg gta act gcc ggg aac ttc aat gca cag cag ctt acg<br>Leu Pro Ser Trp Val Thr Ala Gly Asn Phe Asn Ala Gln Gln Leu Thr<br>            110                    115                        120 | 538 |
| cag atc atc caa aac cac tgc ggc acg gtc gtc gga cac tac aag gga<br>Gln Ile Ile Gln Asn His Cys Gly Thr Val Val Gly His Tyr Lys Gly<br>       125                    130                        135 | 586 |
| caa gt   gtgagtgttg gccatatccg ccgacgtgta tcgtgtgctg accgtgtttt<br>Gln Val<br>140 | 641 |
| atag t tgt ac   gtgacgcttg ttgcttgatc gtatgaatcc acttagctga<br>        Cys Thr | 691 |
| ctcgacgcag t gag ctg gga tgt a gtaaacggta acggacattc cttctctttg<br>              Glu Leu Gly Cys<br>                    145 | 745 |
| ctacacacaa ctcggactca cactcggctg cag ag   cct ctc aac gac gac ggc<br>                                                        Lys Pro Leu Asn Asp Asp Gly<br>                                                                          150 | 798 |
| tcg ttc cgc cag gac gtg ttc ttc aac act ctc ggc tcg ggc tac atc<br>Ser Phe Arg Gln Asp Val Phe Phe Asn Thr Leu Gly Ser Gly Tyr Ile<br>155                          160                        165                        170 | 846 |
| gcg acg gcg ctc cgc gct gcc agg gcc gca gac cct gcg gcg aag ctg<br>Ala Thr Ala Leu Arg Ala Ala Arg Ala Ala Asp Pro Ala Ala Lys Leu<br>            175                    180                        185 | 894 |
| tac atc aac gag ttt aac gtc gag ggc cta g gttcgtccca ccgtatcccc<br>Tyr Ile Asn Glu Phe Asn Val Glu Gly Leu<br>             190                    195 | 945 |
| gctcattgca tcgtctgagc ccgaatcttc tag gc   gca aag tcg acc gcc ttg<br>                                                    Gly Ala Lys Ser Thr Ala Leu<br>                                                                      200 | 998 |
| aag aac ctc gtc act tcg ctg aag cag cag ggc gtc ccg atc gac ggc<br>Lys Asn Leu Val Thr Ser Leu Lys Gln Gln Gly Val Pro Ile Asp Gly<br>       205                    210                        215 | 1046 |
| gtc ggt ttc cag tgc cac ttc atc gtc ggc cag gtc ccc acg acg ctc<br>Val Gly Phe Gln Cys His Phe Ile Val Gly Gln Val Pro Thr Thr Leu<br>220                          225                        230                        235 | 1094 |
| atc cag agc atg cag cag ttc act gcg ctc ggc ctc gag gtg gcc atc<br>Ile Gln Ser Met Gln Gln Phe Thr Ala Leu Gly Leu Glu Val Ala Ile<br>                          240                        245                        250 | 1142 |

```
acg gag ctc gac atc cgc atg acg ctc cct gaa act gcg gcg ctg ctc     1190
Thr Glu Leu Asp Ile Arg Met Thr Leu Pro Glu Thr Ala Ala Leu Leu
            255                 260                 265 gag cag cag aag cag gac ttc cag act gtt atc cac gcg tgt aag tcc     1238
Glu Gln Gln Lys Gln Asp Phe Gln Thr Val Ile His Ala Cys Lys Ser
        270                 275                 280 gtg gcg ggc tgt gtc ggc gtc act gtg tgg gac ttc acc gat aag         1283
Val Ala Gly Cys Val Gly Val Thr Val Trp Asp Phe Thr Asp Lys
    285                 290                 295 gtatgtcgtt gtcccgcccc ggcgagatgg ttggattagc gtgctcaccg gtattatacc   1343 ag ttc tcc ttc gtg ccg agc acg ttc ccg ggt cag ggt gct gcc act      1390
   Phe Ser Phe Val Pro Ser Thr Phe Pro Gly Gln Gly Ala Ala Thr
       300                 305                 310 cct tgg gat cag gtacgtcccg ccgaaccttg ggccttacaa gctccgggag         1442
Pro Trp Asp Gln
    315 agggctaact gcggatgcgc ag aac ctg gtg aag aag ccg gca ttt gat ggc    1494
                         Asn Leu Val Lys Lys Pro Ala Phe Asp Gly
                             320                 325 atc gtc gcc gga ttc cag cag tga                                     1518
Ile Val Ala Gly Phe Gln Gln
        330

<210> SEQ ID NO 2
<211> LENGTH: 352
<212> TYPE: PRT
<213> ORGANISM: Trametes versicolor

<400> SEQUENCE: 2

Met His Phe Ser Leu Leu Ala Ala Phe Ile Ala Leu Ala Pro Ala Ala
                -15                 -10                  -5

Leu Ala Ile Pro Ala Thr Pro Val Val Asp Ala Ser Leu Pro Gly Ser
        -1   1                   5                  10

Thr Ala Asn Val Ala Gly Leu His Ala Val Ala Lys Ala Ala Gly Lys
 15                  20                  25                  30

Leu Tyr Leu Gly Thr Ala Thr Asp Asn Asn Glu Leu Thr Asn Thr Gln
                 35                  40                  45

Tyr Thr Ala Ile Leu Glu Ala Pro Asn Met Phe Gly Gln Ile Thr Ala
             50                  55                  60

Glu Asn Thr Met Lys Trp Asp Ala Thr Glu Pro Gln Gln Asn Val Phe
 65                  70                  75

Thr Phe Thr Gln Gly Asp Gln Ile Ala Asn Leu Ala Lys Ser His Gly
         80                  85                  90

Met Leu Leu Arg Gly His Asn Cys Val Trp His Gln Gln Leu Pro Ser
 95                 100                 105                 110

Trp Val Thr Ala Gly Asn Phe Asn Ala Gln Gln Leu Thr Gln Ile Ile
                115                 120                 125

Gln Asn His Cys Gly Thr Val Val Gly His Tyr Lys Gly Gln Val Cys
            130                 135                 140

Thr Glu Leu Gly Cys Lys Pro Leu Asn Asp Asp Gly Ser Phe Arg Gln
        145                 150                 155

Asp Val Phe Phe Asn Thr Leu Gly Ser Gly Tyr Ile Ala Thr Ala Leu
    160                 165                 170

Arg Ala Ala Arg Ala Ala Asp Pro Ala Ala Lys Leu Tyr Ile Asn Glu
175                 180                 185                 190

Phe Asn Val Glu Gly Leu Gly Ala Lys Ser Thr Ala Leu Lys Asn Leu
                195                 200                 205
```

```
Val Thr Ser Leu Lys Gln Gln Gly Val Pro Ile Asp Gly Val Gly Phe
            210                 215                 220
Gln Cys His Phe Ile Val Gly Gln Val Pro Thr Thr Leu Ile Gln Ser
            225                 230                 235
Met Gln Gln Phe Thr Ala Leu Gly Leu Glu Val Ala Ile Thr Glu Leu
240                 245                 250
Asp Ile Arg Met Thr Leu Pro Glu Thr Ala Ala Leu Leu Glu Gln Gln
255                 260                 265                 270
Lys Gln Asp Phe Gln Thr Val Ile His Ala Cys Lys Ser Val Ala Gly
                275                 280                 285
Cys Val Gly Val Thr Val Trp Asp Phe Thr Asp Lys Phe Ser Phe Val
            290                 295                 300
Pro Ser Thr Phe Pro Gly Gln Gly Ala Ala Thr Pro Trp Asp Gln Asn
            305                 310                 315
Leu Val Lys Lys Pro Ala Phe Asp Gly Ile Val Ala Gly Phe Gln Gln
320                 325                 330
```

<210> SEQ ID NO 3
<211> LENGTH: 1464
<212> TYPE: DNA
<213> ORGANISM: Trametes versicolor
<220> FEATURE:
<221> NAME/KEY: CDS
<222> LOCATION: (1)..(249)
<220> FEATURE:
<221> NAME/KEY: sig_peptide
<222> LOCATION: (1)..(60)
<220> FEATURE:
<221> NAME/KEY: mat_peptide
<222> LOCATION: (61)..()
<220> FEATURE:
<221> NAME/KEY: Intron
<222> LOCATION: (250)..(306)
<220> FEATURE:
<221> NAME/KEY: CDS
<222> LOCATION: (307)..(524)
<220> FEATURE:
<221> NAME/KEY: Intron
<222> LOCATION: (525)..(648)
<220> FEATURE:
<221> NAME/KEY: CDS
<222> LOCATION: (649)..(665)
<220> FEATURE:
<221> NAME/KEY: Intron
<222> LOCATION: (666)..(720)
<220> FEATURE:
<221> NAME/KEY: CDS
<222> LOCATION: (721)..(867)
<220> FEATURE:
<221> NAME/KEY: Intron
<222> LOCATION: (868)..(929)
<220> FEATURE:
<221> NAME/KEY: CDS
<222> LOCATION: (930)..(1237)
<220> FEATURE:
<221> NAME/KEY: Intron
<222> LOCATION: (1238)..(1294)
<220> FEATURE:
<221> NAME/KEY: CDS
<222> LOCATION: (1295)..(1351)
<220> FEATURE:
<221> NAME/KEY: Intron
<222> LOCATION: (1352)..(1404)
<220> FEATURE:
<221> NAME/KEY: CDS
<222> LOCATION: (1405)..(1461)

<400> SEQUENCE: 3 atg ctc tct ctg tca aaa agc ctt ctt gcg ctc tct gtc ttg gtc cga         48

```
                Met Leu Ser Leu Ser Lys Ser Leu Leu Ala Leu Ser Val Leu Val Arg
                -20             -15                 -10                  -5 ggt gcg ctc gcc gta cct gcc agc gat gcg agt agc gct ctg ttc cca          96
Gly Ala Leu Ala Val Pro Ala Ser Asp Ala Ser Ser Ala Leu Phe Pro
        -1  1                   5                  10 ttg tcg ggg ctg aat ctg gcc gcc aag ggc gcg cgg aag ttg tac ctt         144
Leu Ser Gly Leu Asn Leu Ala Ala Lys Gly Ala Arg Lys Leu Tyr Leu
            15                  20                  25 ggc acg gca acg aac agc gag cag tgg aac gac acg acg tac ttc aac         192
Gly Thr Ala Thr Asn Ser Glu Gln Trp Asn Asp Thr Thr Tyr Phe Asn
            30                  35                  40 atc ctg aag aac aac gcc gag ttc ggg cag gta acg ccc gcg aac gtc         240
Ile Leu Lys Asn Asn Ala Glu Phe Gly Gln Val Thr Pro Ala Asn Val
45                  50                  55                  60 atg aaa tgg gtacgttgtc ggcgtcctct tcgtactgac gatgttgagg                 289
Met Lys Trp ctaactttga cgcatag ttt gcg acg gag cct gag gag ggc gtc ttc acg         339
                   Phe Ala Thr Glu Pro Glu Glu Gly Val Phe Thr
                                   65                  70 ttc cag gac ggg gat atc atc gcg gac ttt acc aaa aag acg ggg aag         387
Phe Gln Asp Gly Asp Ile Ile Ala Asp Phe Thr Lys Lys Thr Gly Lys
75                  80                  85                  90 ctg ctg cgc gga cac aac tgc gtg tgg cac aac cag ctc ccc gac tgg         435
Leu Leu Arg Gly His Asn Cys Val Trp His Asn Gln Leu Pro Asp Trp
                95                  100                 105 cta gaa acc ggc acg ttc agt gcg ccc gag ctc gca ttc att gtc tcg         483
Leu Glu Thr Gly Thr Phe Ser Ala Pro Glu Leu Ala Phe Ile Val Ser
                110                 115                 120 cgg cac tgc ttc aac ctc gtg aac cac tac caa ggc tat gt                  524
Arg His Cys Phe Asn Leu Val Asn His Tyr Gln Gly Tyr Val
                125                 130                 135 gtgagtgcaa ttcgttacct gtgatcctgc tcaacgatct aaatcggtac acggcaggtg       584
tacgtacaag cgtgtcggtg atgtttcatt gaggctgatg gcttattttg gaaaattcag       644 atag c tgg gac gtc atc aat g gttcgtgcta cttgacttcc cggatgtgct           695
       Trp Asp Val Ile Asn
                   140 tgtttccgat ctcgaattt gctag ag gct ttc aac gac gac gga acc ttc           746
                                Glu Ala Phe Asn Asp Asp Gly Thr Phe
                                            145                 150 cgt tcg gat atc ttc ttc gac acg ctc aac aca acc tac atc ccg ctc         794
Arg Ser Asp Ile Phe Phe Asp Thr Leu Asn Thr Thr Tyr Ile Pro Leu
                155                 160                 165 gcc ctc tac gca gca cgc gcc gcg gac ccc aaa gcg aag ctc tac atc         842
Ala Leu Tyr Ala Ala Arg Ala Ala Asp Pro Lys Ala Lys Leu Tyr Ile
                170                 175                 180 aac gac ttc aac atc gaa ggc ata g gtacgccaca taacaccatc                 887
Asn Asp Phe Asn Ile Glu Gly Ile
                185                 190 tgcccgccgc aaagccctgc cacccaacta ccctactcgc ag gt gcg aag tcc           940
                                                 Gly Ala Lys Ser gac gcg ctc aag agt ctc atc aag gag ctc aag agc caa aac gtc ccc         988
Asp Ala Leu Lys Ser Leu Ile Lys Glu Leu Lys Ser Gln Asn Val Pro
195                 200                 205                 210 atc gac ggc gtc ggg ctg cag tcg cac ttc gag gtc ggc ggc gtc ccg        1036
Ile Asp Gly Val Gly Leu Gln Ser His Phe Glu Val Gly Gly Val Pro
                215                 220                 225 ccc acg ctg cag cag aac atg gag gag ttc gtc gcg ctc ggg ctc gag        1084
Pro Thr Leu Gln Gln Asn Met Glu Glu Phe Val Ala Leu Gly Leu Glu
```

```
                  230                 235                 240
gtc gcg atc acg gag ctc gac atc cgc ttc acc gcg ctc ccg ccg acg         1132
Val Ala Ile Thr Glu Leu Asp Ile Arg Phe Thr Ala Leu Pro Pro Thr
            245                 250                 255 cct gca ggc ctc gcg cag cag aag gcg gac tac gag acc gtc gtc gcc         1180
Pro Ala Gly Leu Ala Gln Gln Lys Ala Asp Tyr Glu Thr Val Val Ala
    260                 265                 270 gcg tgc aac gcg gtc ccg aag tgc gtg ggg gtc acg ctg tgg gac ttc         1228
Ala Cys Asn Ala Val Pro Lys Cys Val Gly Val Thr Leu Trp Asp Phe
275                 280                 285                 290 acg gac aag gtgcgtctgc gagattgtgg tcgtgtgatg ggtgttgatg                 1277
Thr Asp Lys ccggatgggc ggggtag tac tcg tgg atc ccg ggg acc ttc cct ggg cag          1327
                    Tyr Ser Trp Ile Pro Gly Thr Phe Pro Gly Gln
                                295                 300 gga gat gcg tgt ccc tgg acg gat gtacgttcct tagtctgtct cgtccgaagg        1381
Gly Asp Ala Cys Pro Trp Thr Asp
305                 310 tgtgatctaa tgatgtacca cag gaa ttt gtg aag agg cca gca tac gag ggc       1434
                       Glu Phe Val Lys Arg Pro Ala Tyr Glu Gly
                                  315                 320 atc atc gag ggg ttc aag gcc cac cat tag                                 1464
Ile Ile Glu Gly Phe Lys Ala His His
    325                 330

<210> SEQ ID NO 4
<211> LENGTH: 351
<212> TYPE: PRT
<213> ORGANISM: Trametes versicolor

<400> SEQUENCE: 4

Met Leu Ser Leu Ser Lys Ser Leu Leu Ala Leu Ser Val Leu Val Arg
-20                 -15                 -10                 -5

Gly Ala Leu Ala Val Pro Ala Ser Asp Ala Ser Ser Ala Leu Phe Pro
        -1  1               5                   10

Leu Ser Gly Leu Asn Leu Ala Ala Lys Gly Ala Arg Lys Leu Tyr Leu
            15                  20                  25

Gly Thr Ala Thr Asn Ser Glu Gln Trp Asn Asp Thr Thr Tyr Phe Asn
    30                  35                  40

Ile Leu Lys Asn Asn Ala Glu Phe Gly Gln Val Thr Pro Ala Asn Val
45                  50                  55                  60

Met Lys Trp Phe Ala Thr Glu Pro Glu Glu Gly Val Phe Thr Phe Gln
            65                  70                  75

Asp Gly Asp Ile Ile Ala Asp Phe Thr Lys Lys Thr Gly Lys Leu Leu
    80                  85                  90

Arg Gly His Asn Cys Val Trp His Asn Gln Leu Pro Asp Trp Leu Glu
            95                  100                 105

Thr Gly Thr Phe Ser Ala Pro Glu Leu Ala Phe Ile Val Ser Arg His
    110                 115                 120

Cys Phe Asn Leu Val Asn His Tyr Gln Gly Tyr Val Trp Asp Val Ile
125                 130                 135                 140

Asn Glu Ala Phe Asn Asp Asp Gly Thr Phe Arg Ser Asp Ile Phe Phe
            145                 150                 155

Asp Thr Leu Asn Thr Thr Tyr Ile Pro Leu Ala Leu Tyr Ala Ala Arg
    160                 165                 170

Ala Ala Asp Pro Lys Ala Lys Leu Tyr Ile Asn Asp Phe Asn Ile Glu
175                 180                 185
```

-continued

```
Gly Ile Gly Ala Lys Ser Asp Ala Leu Lys Ser Leu Ile Lys Glu Leu
            190                 195                 200

Lys Ser Gln Asn Val Pro Ile Asp Gly Val Gly Leu Gln Ser His Phe
205                 210                 215                 220

Glu Val Gly Gly Val Pro Pro Thr Leu Gln Gln Asn Met Glu Glu Phe
                225                 230                 235

Val Ala Leu Gly Leu Glu Val Ala Ile Thr Glu Leu Asp Ile Arg Phe
            240                 245                 250

Thr Ala Leu Pro Pro Thr Pro Ala Gly Leu Ala Gln Gln Lys Ala Asp
                255                 260                 265

Tyr Glu Thr Val Val Ala Ala Cys Asn Ala Val Pro Lys Cys Val Gly
            270                 275                 280

Val Thr Leu Trp Asp Phe Thr Asp Lys Tyr Ser Trp Ile Pro Gly Thr
285                 290                 295                 300

Phe Pro Gly Gln Gly Asp Ala Cys Pro Trp Thr Asp Glu Phe Val Lys
                305                 310                 315

Arg Pro Ala Tyr Glu Gly Ile Ile Glu Gly Phe Lys Ala His His
                320                 325                 330

<210> SEQ ID NO 5
<211> LENGTH: 1533
<212> TYPE: DNA
<213> ORGANISM: Trametes versicolor
<220> FEATURE:
<221> NAME/KEY: CDS
<222> LOCATION: (1)..(273)
<220> FEATURE:
<221> NAME/KEY: sig_peptide
<222> LOCATION: (1)..(69)
<220> FEATURE:
<221> NAME/KEY: mat_peptide
<222> LOCATION: (70)..()
<220> FEATURE:
<221> NAME/KEY: Intron
<222> LOCATION: (274)..(324)
<220> FEATURE:
<221> NAME/KEY: CDS
<222> LOCATION: (325)..(430)
<220> FEATURE:
<221> NAME/KEY: Intron
<222> LOCATION: (431)..(471)
<220> FEATURE:
<221> NAME/KEY: CDS
<222> LOCATION: (472)..(598)
<220> FEATURE:
<221> NAME/KEY: Intron
<222> LOCATION: (599)..(717)
<220> FEATURE:
<221> NAME/KEY: CDS
<222> LOCATION: (718)..(734)
<220> FEATURE:
<221> NAME/KEY: Intron
<222> LOCATION: (735)..(788)
<220> FEATURE:
<221> NAME/KEY: CDS
<222> LOCATION: (789)..(935)
<220> FEATURE:
<221> NAME/KEY: Intron
<222> LOCATION: (936)..(989)
<220> FEATURE:
<221> NAME/KEY: CDS
<222> LOCATION: (990)..(1297)
<220> FEATURE:
<221> NAME/KEY: Intron
<222> LOCATION: (1298)..(1352)
<220> FEATURE:
<221> NAME/KEY: CDS
<222> LOCATION: (1353)..(1400)
```

```
<400> SEQUENCE: 5 atg atg acg aac ttc cac cta gtc tcc tcg ttg atc gcg ctc gcg ttt        48
Met Met Thr Asn Phe His Leu Val Ser Ser Leu Ile Ala Leu Ala Phe
        -20                 -15                 -10 ctt tcg ctg acc ggc tta gca tcc att ccg tcg aca cgc gct ctg gct        96
Leu Ser Leu Thr Gly Leu Ala Ser Ile Pro Ser Thr Arg Ala Leu Ala
 -5              -1   1               5 gga aat tcc tcg agg atc aat tct cct tct ggc ttg aac ttg gcg gct       144
Gly Asn Ser Ser Arg Ile Asn Ser Pro Ser Gly Leu Asn Leu Ala Ala
 10                  15                  20                  25 ttg gaa gcc cgg aag ctg tac ttt ggt act gcg acc aac aac gtc gag       192
Leu Glu Ala Arg Lys Leu Tyr Phe Gly Thr Ala Thr Asn Asn Val Glu
             30                  35                  40 ctc aac gac acg gca tac ttc gac att ctc gat gat ttc aaa atg ttc       240
Leu Asn Asp Thr Ala Tyr Phe Asp Ile Leu Asp Asp Phe Lys Met Phe
 45                  50                  55 ggt caa att acg ccc gcc aaa ggc atg aaa tgg gtccgttctc caacttctgc     293
Gly Gln Ile Thr Pro Ala Lys Gly Met Lys Trp
 60                  65 atcataaatc gctcgctgat tgttttggaa g atg gag acg gaa cct gag cga        345
                                  Met Glu Thr Glu Pro Glu Arg
                                           70              75 ggc gtt ttc acc ttc gcg cag gca gac caa atc gcg caa ctt gcc agc       393
Gly Val Phe Thr Phe Ala Gln Ala Asp Gln Ile Ala Gln Leu Ala Ser
             80                  85                  90 gag ggc gga aag ctg ttg aga ggc tcg tac tcg aaa g gtccctcgct          440
Glu Gly Gly Lys Leu Leu Arg Gly Ser Tyr Ser Lys
         95                 100 accccatacg tgctaacatt ccgttctgca g gc  cac aac tgc gta tgg tat       491
                                      Gly His Asn Cys Val Trp Tyr
                                          105             110 aat gcg ctt ccc ggg tgg gtc aca aat acc acg tgg acg gcc tcc gag       539
Asn Ala Leu Pro Gly Trp Val Thr Asn Thr Thr Trp Thr Ala Ser Glu
         115                 120                 125 atg gcc gag gtc gta cag gag cat tgt ttc aac atc gtc cgt tac tgg       587
Met Ala Glu Val Val Gln Glu His Cys Phe Asn Ile Val Arg Tyr Trp
 130                 135                 140 caa gga caa gc  gtgagtaccg atctctctca ttaatatcgt gtctctcaat          638
Gln Gly Gln Ala
145 ttttattccg agtagatgtg agtatcaacg ccttccggag gaatcccgct gaacataggc     698 cgtcctttta cacagacag c tgg gac gtt att aac g gtgagttgct              744
                      Trp Asp Val Ile Asn
                         150 cgagattgaa ggcagctgcc cgtagcttac accatttccc gcag ag  cca ttc aac     799
                                                    Glu Pro Phe Asn
                                                            155 gat gac gga acg tgg cgc gag acc atg tgg ttt aat act ctc aac acg       847
Asp Asp Gly Thr Trp Arg Glu Thr Met Trp Phe Asn Thr Leu Asn Thr
         160                 165                 170 agc tac att ccg ctc gcg ttg cac gct gcg cgc gcg gcc gat cct cat       895
Ser Tyr Ile Pro Leu Ala Leu His Ala Ala Arg Ala Ala Asp Pro His
         175                 180                 185 act aag ctg tac atc aat gag tac aat atc acc gga aca g gtgcgtcgta    945
Thr Lys Leu Tyr Ile Asn Glu Tyr Asn Ile Thr Gly Thr
     190                 195                 200 cgcctcacgc tcagactatg cctccttcat cattcagtat acag gc  ccg aag gcg   1000
                                                     Gly Pro Lys Ala
```

```
acg tcc atg aag aac ctc atc aaa gac ttg aag cgc gct ggt gtg ccc    1048
Thr Ser Met Lys Asn Leu Ile Lys Asp Leu Lys Arg Ala Gly Val Pro
205             210                 215                 220 gtt cac ggc gtt gga gtt caa gcg cac gag acc gtc ggg gaa gtt ccg    1096
Val His Gly Val Gly Val Gln Ala His Glu Thr Val Gly Glu Val Pro
                225                 230                 235 acc gac atc cgc aag aac ctc ggg gag ttc gtc gca ctc ggc gtc gag    1144
Thr Asp Ile Arg Lys Asn Leu Gly Glu Phe Val Ala Leu Gly Val Glu
                240                 245                 250 gtc gcg atc aca gaa ctc gac atc aag ttc aac acg ctt cct cct gat    1192
Val Ala Ile Thr Glu Leu Asp Ile Lys Phe Asn Thr Leu Pro Pro Asp
            255                 260                 265 gca gcc ggg ctc aaa caa cag aag cga gat tac gaa gct att gtc tcg    1240
Ala Ala Gly Leu Lys Gln Gln Lys Arg Asp Tyr Glu Ala Ile Val Ser
        270                 275                 280 gcg tgc gcg gag gta aaa gga tgt gtg ggc gtg acg gtt tgg gac ttc    1288
Ala Cys Ala Glu Val Lys Gly Cys Val Gly Val Thr Val Trp Asp Phe
285                 290                 295                 300 acg gac aag gtgggaaagt attcgacttc acgaagcaat accaagtatt           1337
Thr Asp Lys cacctttgcg tacag tac tca tgg atc ccc gga acg ttc cct gga acc ggc    1388
              Tyr Ser Trp Ile Pro Gly Thr Phe Pro Gly Thr Gly
                305                 310                 315 gat gct tgt cct tgagacgatg tgagcgtgat gctattgcgt attgcttttt       1440
Asp Ala Cys Pro ctactgactg tctctcgtac ttctttgtct caggatttgc acaagaagcc ggcgtactat  1500
ggaattttgg acgggtttgg gagatctcgc tga                              1533

<210> SEQ ID NO 6
<211> LENGTH: 342
<212> TYPE: PRT
<213> ORGANISM: Trametes versicolor

<400> SEQUENCE: 6

Met Met Thr Asn Phe His Leu Val Ser Ser Leu Ile Ala Leu Ala Phe
            -20                 -15                 -10

Leu Ser Leu Thr Gly Leu Ala Ser Ile Pro Ser Thr Arg Ala Leu Ala
 -5                  -1  1               5

Gly Asn Ser Ser Arg Ile Asn Ser Pro Ser Gly Leu Asn Leu Ala Ala
10                  15                  20                  25

Leu Glu Ala Arg Lys Leu Tyr Phe Gly Thr Ala Thr Asn Asn Val Glu
                30                  35                  40

Leu Asn Asp Thr Ala Tyr Phe Asp Ile Leu Asp Asp Phe Lys Met Phe
            45                  50                  55

Gly Gln Ile Thr Pro Ala Lys Gly Met Lys Trp Met Glu Thr Glu Pro
        60                  65                  70

Glu Arg Gly Val Phe Thr Phe Ala Gln Ala Asp Gln Ile Ala Gln Leu
    75                  80                  85

Ala Ser Glu Gly Gly Lys Leu Leu Arg Gly Ser Tyr Ser Lys Gly His
90                  95                  100                 105

Asn Cys Val Trp Tyr Asn Ala Leu Pro Gly Trp Val Thr Asn Thr Thr
                110                 115                 120

Trp Thr Ala Ser Glu Met Ala Glu Val Val Gln Glu His Cys Phe Asn
            125                 130                 135

Ile Val Arg Tyr Trp Gln Gly Gln Ala Trp Asp Val Ile Asn Glu Pro
        140                 145                 150
```

```
              Phe Asn Asp Asp Gly Thr Trp Arg Glu Thr Met Trp Phe Asn Thr Leu
              155                 160                 165

Asn Thr Ser Tyr Ile Pro Leu Ala Leu His Ala Ala Arg Ala Ala Asp
170                 175                 180                 185

Pro His Thr Lys Leu Tyr Ile Asn Glu Tyr Asn Ile Thr Gly Thr Gly
                190                 195                 200

Pro Lys Ala Thr Ser Met Lys Asn Leu Ile Lys Asp Leu Lys Arg Ala
            205                 210                 215

Gly Val Pro Val His Gly Val Gln Ala His Glu Thr Val Gly
        220                 225                 230

Glu Val Pro Thr Asp Ile Arg Lys Asn Leu Gly Glu Phe Val Ala Leu
235                 240                 245

Gly Val Glu Val Ala Ile Thr Glu Leu Asp Ile Lys Phe Asn Thr Leu
250                 255                 260                 265

Pro Pro Asp Ala Ala Gly Leu Lys Gln Gln Lys Arg Asp Tyr Glu Ala
                270                 275                 280

Ile Val Ser Ala Cys Ala Glu Val Lys Gly Cys Val Gly Val Thr Val
            285                 290                 295

Trp Asp Phe Thr Asp Lys Tyr Ser Trp Ile Pro Gly Thr Phe Pro Gly
        300                 305                 310

Thr Gly Asp Ala Cys Pro
    315

<210> SEQ ID NO 7
<211> LENGTH: 1668
<212> TYPE: DNA
<213> ORGANISM: Trametes versicolor
<220> FEATURE:
<221> NAME/KEY: CDS
<222> LOCATION: (1)..(174)
<220> FEATURE:
<221> NAME/KEY: sig_peptide
<222> LOCATION: (1)..(57)
<220> FEATURE:
<221> NAME/KEY: mat_peptide
<222> LOCATION: (58)..()
<220> FEATURE:
<221> NAME/KEY: Intron
<222> LOCATION: (175)..(240)
<220> FEATURE:
<221> NAME/KEY: CDS
<222> LOCATION: (241)..(453)
<220> FEATURE:
<221> NAME/KEY: Intron
<222> LOCATION: (454)..(510)
<220> FEATURE:
<221> NAME/KEY: CDS
<222> LOCATION: (511)..(728)
<220> FEATURE:
<221> NAME/KEY: Intron
<222> LOCATION: (729)..(785)
<220> FEATURE:
<221> NAME/KEY: CDS
<222> LOCATION: (786)..(787)
<220> FEATURE:
<221> NAME/KEY: Intron
<222> LOCATION: (788)..(844)
<220> FEATURE:
<221> NAME/KEY: CDS
<222> LOCATION: (845)..(865)
<220> FEATURE:
<221> NAME/KEY: Intron
<222> LOCATION: (866)..(922)
<220> FEATURE:
<221> NAME/KEY: CDS
<222> LOCATION: (923)..(1069)
<220> FEATURE:
<221> NAME/KEY: Intron
```

```
<222> LOCATION: (1070)..(1136)
<220> FEATURE:
<221> NAME/KEY: CDS
<222> LOCATION: (1137)..(1441)
<220> FEATURE:
<221> NAME/KEY: Intron
<222> LOCATION: (1442)..(1502)
<220> FEATURE:
<221> NAME/KEY: CDS
<222> LOCATION: (1503)..(1559)
<220> FEATURE:
<221> NAME/KEY: Intron
<222> LOCATION: (1560)..(1617)
<220> FEATURE:
<221> NAME/KEY: CDS
<222> LOCATION: (1618)..(1665)

<400> SEQUENCE: 7
```

| | | | | | | | | | | | | | | | | |
|---|---|---|---|---|---|---|---|---|---|---|---|---|---|---|---|---|
| atg | aac | ctc | tca | gcg | tcg | ttc | gca | gta | ctt | gtc | gct | ctg | atc | ccg | tac | 48 |
| Met | Asn | Leu | Ser | Ala | Ser | Phe | Ala | Val | Leu | Val | Ala | Leu | Ile | Pro | Tyr | |
| | | | -15 | | | | | -10 | | | | | -5 | | | |
| gcc | ctc | gcg | cag | tcc | ccg | gag | tgg | ggc | caa | tgc | ggc | gga | aca | ggc | tat | 96 |
| Ala | Leu | Ala | Gln | Ser | Pro | Glu | Trp | Gly | Gln | Cys | Gly | Gly | Thr | Gly | Tyr | |
| | -1 | 1 | | | 5 | | | | | 10 | | | | | | |
| acg | ggc | gcc | acg | act | tgc | gtg | tcc | gga | acg | gta | tgc | acg | gtg | atc | aac | 144 |
| Thr | Gly | Ala | Thr | Thr | Cys | Val | Ser | Gly | Thr | Val | Cys | Thr | Val | Ile | Asn | |
| | 15 | | | | 20 | | | | | 25 | | | | | | |

```
ccg tac tac tca caa tgt ctc gca ggc act gtaagtacac gacacacgca          194
Pro Tyr Tyr Ser Gln Cys Leu Ala Gly Thr
 30              35 tctttgtcag gtcacagggg agccaaacgc tgacggtcac ctcaag gcc aca tcc         249
                                                  Ala Thr Ser
                                                   40 gcg cct tcc gct ccc agc cca act gtg agc acc ggc gca ccc gcc ccg        297
Ala Pro Ser Ala Pro Ser Pro Thr Val Ser Thr Gly Ala Pro Ala Pro
    45                  50                  55 agc gtc agc ggt ctg cac act ctc gcc aaa gcc gct ggg aag ctc tac        345
Ser Val Ser Gly Leu His Thr Leu Ala Lys Ala Ala Gly Lys Leu Tyr
 60                  65                  70 ttt ggc agc gcg acg gac aac ccc gag ctg acc gac acc gcc tac gtc        393
Phe Gly Ser Ala Thr Asp Asn Pro Glu Leu Thr Asp Thr Ala Tyr Val
 75                  80                  85                  90 gcg aag ctc agc gac aac gcc gag ttc ggc cag atc acc ccc ggt aac        441
Ala Lys Leu Ser Asp Asn Ala Glu Phe Gly Gln Ile Thr Pro Gly Asn
                 95                 100                 105 agc atg aaa tgg gtgagtaccg caccctccat ccccattctc aggtttgtga           493
Ser Met Lys Trp
         110 gaatgaatgc gtcgtag gac gcg acg gag ccg acg cgg ggg acg ttc acg        543
                   Asp Ala Thr Glu Pro Thr Arg Gly Thr Phe Thr
                                115                 120 ttc acg ggc ggg gac gtg gtt gcg agc ctg gcg gag aag aac ggg cag        591
Phe Thr Gly Gly Asp Val Val Ala Ser Leu Ala Glu Lys Asn Gly Gln
            125                 130                 135 ctg ctg cgc ggg cac aac tgc gtg tgg tac aac cag ctc ccg agc tgg        639
Leu Leu Arg Gly His Asn Cys Val Trp Tyr Asn Gln Leu Pro Ser Trp
        140                 145                 150 gtc gcg aac ggg cag ttc acg gct gcg gat ttg acg gac gtg atc acg        687
Val Ala Asn Gly Gln Phe Thr Ala Ala Asp Leu Thr Asp Val Ile Thr
    155                 160                 165 acg cac tgc ggc acg ctc gtt ggc cac tac aag gga caa at                728
Thr His Cys Gly Thr Leu Val Gly His Tyr Lys Gly Gln Ile
170                 175                 180
```

```
gtgagtgccg tcttactct cgaataatcg tgttacagta tgctaatgga ggcgcag c      786 t gtacgcatca tagggttgtt cgtgactgtt gctggtactg acttgctcgt accgaag     844 ac  tct tgg gac gtc atc aat g gtcagttgtc gtgagcgaga tcgtgcatta       895
    Tyr Ser Trp Asp Val Ile Asn
    185                 190 cagtatgctc aatattttcg tgcctag aa  ccc ttt aac gac gac ggt acc tgg    948
                                  Glu Pro Phe Asn Asp Asp Gly Thr Trp
                                                          195 cgc tcg gat gtg ttc ttc aat acg ctc ggt cag tcc tac gtc tcc atc      996
Arg Ser Asp Val Phe Phe Asn Thr Leu Gly Gln Ser Tyr Val Ser Ile
200                 205                 210                 215 gcg ctc aaa gcc gca cgc gct gca gac ccc aac gcc aag ctc tac atc     1044
Ala Leu Lys Ala Ala Arg Ala Ala Asp Pro Asn Ala Lys Leu Tyr Ile
                220                 225                 230 aac gac tac aac atc gag cag acc g gtgcgcccct cctttccttg             1089
Asn Asp Tyr Asn Ile Glu Gln Thr
                235 atacttccct tagcaccatc aaactaaccc tgcatatgat cgcacag gc  gcg aag     1144
                                                       Gly Ala Lys
                                                               240 tcg acc gcg atg ctg aac ctc gtg aag cag cta caa gca gac ggc gtg     1192
Ser Thr Ala Met Leu Asn Leu Val Lys Gln Leu Gln Ala Asp Gly Val
         245                 250                 255 cca atc gac ggc gtc ggc ttc cag agc cac ttc atc gtt ggc gag gtc     1240
Pro Ile Asp Gly Val Gly Phe Gln Ser His Phe Ile Val Gly Glu Val
    260                 265                 270 ccc ggc tcg ttc cag acc gtg ctc gag cag ttc acc gcg ctc ggg ctc     1288
Pro Gly Ser Phe Gln Thr Val Leu Glu Gln Phe Thr Ala Leu Gly Leu
275                 280                 285                 290 gag gtc gcg atc acg gag ctc gac atc cgc atg acg ctc ccc gcg acg     1336
Glu Val Ala Ile Thr Glu Leu Asp Ile Arg Met Thr Leu Pro Ala Thr
                295                 300                 305 gac gcg ctc ctc gcg cag cag cag aag gac tac cag agc gtc gtg cag     1384
Asp Ala Leu Leu Ala Gln Gln Gln Lys Asp Tyr Gln Ser Val Val Gln
                310                 315                 320 gcg tgc atg aac gtg cag ggc tgt gtg ggc gtc acg atc tgg gac tgg     1432
Ala Cys Met Asn Val Gln Gly Cys Val Gly Val Thr Ile Trp Asp Trp
                325                 330                 335 acg gac aag gtgcgtgtgg tggggtggag agagcgagcg aggagggtgc             1481
Thr Asp Lys
        340 tgatagggac tcttggggca g tac tcg tgg gtg ccg tcg acg ttc tcg gga     1532
                       Tyr Ser Trp Val Pro Ser Thr Phe Ser Gly
                                       345                 350 cag ggc gcg gct ctg cct tgg gac gag gtgggtggtc ctctcccgcg           1579
Gln Gly Ala Ala Leu Pro Trp Asp Glu
            355                 360 ttctggggat actcaatgga cgcatttacg ttcgtcag acc ttc aac aaa aag ccc   1635
                                          Thr Phe Asn Lys Lys Pro
                                                              365 gca tac agc ggc atc acg gcg gca ctg acg tga                         1668
Ala Tyr Ser Gly Ile Thr Ala Ala Leu Thr
        370                 375

<210> SEQ ID NO 8
<211> LENGTH: 395
<212> TYPE: PRT
<213> ORGANISM: Trametes versicolor

<400> SEQUENCE: 8
```

```
Met Asn Leu Ser Ala Ser Phe Ala Val Leu Val Ala Leu Ile Pro Tyr
            -15                 -10                 -5

Ala Leu Ala Gln Ser Pro Glu Trp Gly Gln Cys Gly Gly Thr Gly Tyr
        -1   1               5                  10

Thr Gly Ala Thr Thr Cys Val Ser Gly Thr Val Cys Thr Val Ile Asn
         15              20                  25

Pro Tyr Tyr Ser Gln Cys Leu Ala Gly Thr Thr Ser Ala Pro Ser
 30              35                  40                  45

Ala Pro Ser Pro Thr Val Ser Thr Gly Ala Pro Ala Pro Ser Val Ser
             50                  55                  60

Gly Leu His Thr Leu Ala Lys Ala Ala Gly Lys Leu Tyr Phe Gly Ser
             65                  70                  75

Ala Thr Asp Asn Pro Glu Leu Thr Asp Thr Ala Tyr Val Ala Lys Leu
             80                  85                  90

Ser Asp Asn Ala Glu Phe Gly Gln Ile Thr Pro Gly Asn Ser Met Lys
             95                 100                 105

Trp Asp Ala Thr Glu Pro Thr Arg Gly Thr Phe Thr Phe Thr Gly Gly
110                 115                 120                 125

Asp Val Val Ala Ser Leu Ala Glu Lys Asn Gly Gln Leu Leu Arg Gly
                130                 135                 140

His Asn Cys Val Trp Tyr Asn Gln Leu Pro Ser Trp Val Ala Asn Gly
                145                 150                 155

Gln Phe Thr Ala Ala Asp Leu Thr Asp Val Ile Thr Thr His Cys Gly
                160                 165                 170

Thr Leu Val Gly His Tyr Lys Gly Gln Ile Tyr Ser Trp Asp Val Ile
        175                 180                 185

Asn Glu Pro Phe Asn Asp Asp Gly Thr Trp Arg Ser Asp Val Phe Phe
190                 195                 200                 205

Asn Thr Leu Gly Gln Ser Tyr Val Ser Ile Ala Leu Lys Ala Ala Arg
                210                 215                 220

Ala Ala Asp Pro Asn Ala Lys Leu Tyr Ile Asn Asp Tyr Asn Ile Glu
                225                 230                 235

Gln Thr Gly Ala Lys Ser Thr Ala Met Leu Asn Leu Val Lys Gln Leu
                240                 245                 250

Gln Ala Asp Gly Val Pro Ile Asp Gly Val Gly Phe Gln Ser His Phe
                255                 260                 265

Ile Val Gly Glu Val Pro Gly Ser Phe Gln Thr Val Leu Glu Gln Phe
270                 275                 280                 285

Thr Ala Leu Gly Leu Glu Val Ala Ile Thr Glu Leu Asp Ile Arg Met
                290                 295                 300

Thr Leu Pro Ala Thr Asp Ala Leu Leu Ala Gln Gln Lys Asp Tyr
                305                 310                 315

Gln Ser Val Val Gln Ala Cys Met Asn Val Gln Gly Cys Val Gly Val
                320                 325                 330

Thr Ile Trp Asp Trp Thr Asp Lys Tyr Ser Trp Val Pro Ser Thr Phe
                335                 340                 345

Ser Gly Gln Gly Ala Ala Leu Pro Trp Asp Glu Thr Phe Asn Lys Lys
350                 355                 360                 365

Pro Ala Tyr Ser Gly Ile Thr Ala Ala Leu Thr
                370                 375

<210> SEQ ID NO 9
<211> LENGTH: 1617
```

```
<212> TYPE: DNA
<213> ORGANISM: Trametes versicolor
<220> FEATURE:
<221> NAME/KEY: CDS
<222> LOCATION: (1)..(174)
<220> FEATURE:
<221> NAME/KEY: sig_peptide
<222> LOCATION: (1)..(57)
<220> FEATURE:
<221> NAME/KEY: mat_peptide
<222> LOCATION: (58)..()
<220> FEATURE:
<221> NAME/KEY: Intron
<222> LOCATION: (175)..(231)
<220> FEATURE:
<221> NAME/KEY: CDS
<222> LOCATION: (232)..(459)
<220> FEATURE:
<221> NAME/KEY: Intron
<222> LOCATION: (460)..(525)
<220> FEATURE:
<221> NAME/KEY: CDS
<222> LOCATION: (526)..(743)
<220> FEATURE:
<221> NAME/KEY: Intron
<222> LOCATION: (744)..(798)
<220> FEATURE:
<221> NAME/KEY: CDS
<222> LOCATION: (799)..(800)
<220> FEATURE:
<221> NAME/KEY: Intron
<222> LOCATION: (801)..(858)
<220> FEATURE:
<221> NAME/KEY: CDS
<222> LOCATION: (859)..(879)
<220> FEATURE:
<221> NAME/KEY: Intron
<222> LOCATION: (880)..(935)
<220> FEATURE:
<221> NAME/KEY: CDS
<222> LOCATION: (936)..(1082)
<220> FEATURE:
<221> NAME/KEY: Intron
<222> LOCATION: (1083)..(1142)
<220> FEATURE:
<221> NAME/KEY: CDS
<222> LOCATION: (1143)..(1447)
<220> FEATURE:
<221> NAME/KEY: Intron
<222> LOCATION: (1448)..(1506)
<220> FEATURE:
<221> NAME/KEY: CDS
<222> LOCATION: (1507)..(1614)

<400> SEQUENCE: 9 atg cag ctc tcg acg acc ttc acc ctc ctc gcc gcg atc att ccg ttc      48
Met Gln Leu Ser Thr Thr Phe Thr Leu Leu Ala Ala Ile Ile Pro Phe
        -15                 -10                 -5 gcc ctc ggg cag gcc gcg gag tgg ggc cag tgc ggt ggc att ggc tgg      96
Ala Leu Gly Gln Ala Ala Glu Trp Gly Gln Cys Gly Gly Ile Gly Trp
    -1   1               5                   10 acc ggc gcg acg acg tgc gtg gcg ggc acc acc tgc acg gtc atg aac     144
Thr Gly Ala Thr Thr Cys Val Ala Gly Thr Thr Cys Thr Val Met Asn
 15                  20                  25 gcg tac tac tcc cag tgc ctc ccc ggt tct gtgagtggct gtgctgtggt       194
Ala Tyr Tyr Ser Gln Cys Leu Pro Gly Ser
 30              35 agagacgttc aacatgctga ccggtgaatg cttgtag gct gcg ccc gcg ccg acg    249
                                        Ala Ala Pro Ala Pro Thr
                                                40          45 acg acc ccc acc tcg cct tcg agc ccg gcg acc ccg ccg tcg gcg cct     297
Thr Thr Pro Thr Ser Pro Ser Ser Pro Ala Thr Pro Pro Ser Ala Pro
                 50                  55                  60
```

```
gcg cca acc ggc agc ggc ctc aac aag ctc gcg aag gcg gct ggc aag      345
Ala Pro Thr Gly Ser Gly Leu Asn Lys Leu Ala Lys Ala Ala Gly Lys
         65                  70                  75 ctc tac ctc ggc act gcg acg gac aac agc gag ctc acc gat gcg gcg      393
Leu Tyr Leu Gly Thr Ala Thr Asp Asn Ser Glu Leu Thr Asp Ala Ala
         80                  85                  90 tac acc gcc atc ctc gac gac aac tcc cag ttc ggc cag atc acg ccc      441
Tyr Thr Ala Ile Leu Asp Asp Asn Ser Gln Phe Gly Gln Ile Thr Pro
         95                 100                 105 gcc aac agc atg aaa tgg gtgcgcatta tccctgcatc gtgtactaga             489
Ala Asn Ser Met Lys Trp
110             115 acgctccttg cttattgttg taaaattgga atgcag gac gcg aca gag ccg act      543
                                       Asp Ala Thr Glu Pro Thr
                                                       120 cgc gga acg ttc acg ttc tcg ggt ggt gac cag atc gcg aac ctg gcg      591
Arg Gly Thr Phe Thr Phe Ser Gly Gly Asp Gln Ile Ala Asn Leu Ala
                125                 130                 135 aag acg aac ggg atg ctt ctc cgt gga cac aac tgc gtg tgg tac aac      639
Lys Thr Asn Gly Met Leu Leu Arg Gly His Asn Cys Val Trp Tyr Asn
        140                 145                 150 cag ctc ccg agc tgg gtt gcg aac ggc cag ttc acc gcc gcg gac ctc      687
Gln Leu Pro Ser Trp Val Ala Asn Gly Gln Phe Thr Ala Ala Asp Leu
        155                 160                 165 acg acc gtc atc cag acg cac tgc agc acc ctc gtc agc cac tac aag      735
Thr Thr Val Ile Gln Thr His Cys Ser Thr Leu Val Ser His Tyr Lys
170                 175                 180                 185 ggt caa gt  gtacgtgatt ccttctgtgt atctactctc ccaatactga              783
Gly Gln Val ccccattttc cgcag t t gtacgtctac gttcgcattt atgattcttg tatgcatact     840
gaccgacatg acaaaaag ac  tcc tgg gac gtc gtc aac g gttagtggta         889
                        Tyr Ser Trp Asp Val Val Asn
                                190                 195 ttactccaca agttcaccag ggaagtgttc tgacagtgat ctccag ag  ccg ttc       943
                                                      Glu Pro Phe aac gac gat ggt acc tgg cgc tcg gac gtg ttc tac aac acg ctc ggc      991
Asn Asp Asp Gly Thr Trp Arg Ser Asp Val Phe Tyr Asn Thr Leu Gly
        200                 205                 210 act tcg tac gtg ccc atc gcg ctc aag gct gcg cgc gct gcg gac cct     1039
Thr Ser Tyr Val Pro Ile Ala Leu Lys Ala Ala Arg Ala Ala Asp Pro
215                 220                 225                 230 agc gcc aaa ctc tac atc aac gac tac aac att gag cag acg g           1082
Ser Ala Lys Leu Tyr Ile Asn Asp Tyr Asn Ile Glu Gln Thr
                235                 240 gtaggtcccc agcatccatc tcccaggagt gacgccgctc acggcacaca cgcaccacag   1142 gc  gcc aag gcg acc gcg atg ctg aac ctc gtg aag cag ctc atc gcc    1189
Gly Ala Lys Ala Thr Ala Met Leu Asn Leu Val Lys Gln Leu Ile Ala
245                 250                 255                 260 gac ggc gtt ccg atc gac ggt gtc ggc ttc cag tgc cac ttt atc gtt    1237
Asp Gly Val Pro Ile Asp Gly Val Gly Phe Gln Cys His Phe Ile Val
                265                 270                 275 ggc gag gtc ccc ggc tcg ttc cag acc gtg ctc gag cag ttc acc gcg    1285
Gly Glu Val Pro Gly Ser Phe Gln Thr Val Leu Glu Gln Phe Thr Ala
                280                 285                 290 ctc ggg ctc gag gtc gcg atc acg gag ctc gac atc cgc acg acg acg    1333
Leu Gly Leu Glu Val Ala Ile Thr Glu Leu Asp Ile Arg Thr Thr Thr
        295                 300                 305
```

```
ccc gcg tcg cag tcc gcg ctc gca cag cag gag aag gac tac cag tcg      1381
Pro Ala Ser Gln Ser Ala Leu Ala Gln Gln Glu Lys Asp Tyr Gln Ser
    310             315             320 gtt atc cag gcg tgc atg aac gtc aag ggc tgc gtt ggt gcc acc ctc      1429
Val Ile Gln Ala Cys Met Asn Val Lys Gly Cys Val Gly Ala Thr Leu
325             330             335             340 tgg gac ttc acc gac aag gttcgtaggc aagctttcta cgcgtgtaag             1477
Trp Asp Phe Thr Asp Lys
                345 acgaattggc tgacgctctt gcgatgcag tac tcc tgg gtc ccc tcg acg ttc      1530
                               Tyr Ser Trp Val Pro Ser Thr Phe
                                   350 tcc ggc caa ggt gcg gcg tgc cct tgg gac cag aac ctc gtc aag aag      1578
Ser Gly Gln Gly Ala Ala Cys Pro Trp Asp Gln Asn Leu Val Lys Lys
355             360             365             370 ccc gcg tac act ggt atc gtc aac gct ctc agc gcg tga                  1617
Pro Ala Tyr Thr Gly Ile Val Asn Ala Leu Ser Ala
            375             380

<210> SEQ ID NO 10
<211> LENGTH: 401
<212> TYPE: PRT
<213> ORGANISM: Trametes versicolor

<400> SEQUENCE: 10

Met Gln Leu Ser Thr Thr Phe Thr Leu Leu Ala Ala Ile Ile Pro Phe
            -15                 -10                 -5

Ala Leu Gly Gln Ala Ala Glu Trp Gly Gln Cys Gly Gly Ile Gly Trp
        -1  1               5                   10

Thr Gly Ala Thr Thr Cys Val Ala Gly Thr Thr Cys Thr Val Met Asn
    15                  20                  25

Ala Tyr Tyr Ser Gln Cys Leu Pro Gly Ser Ala Ala Pro Ala Pro Thr
30                  35                  40                  45

Thr Thr Pro Thr Ser Pro Ser Pro Ala Thr Pro Pro Ser Ala Pro
                50                  55                  60

Ala Pro Thr Gly Ser Gly Leu Asn Lys Leu Ala Lys Ala Ala Gly Lys
                65                  70                  75

Leu Tyr Leu Gly Thr Ala Thr Asp Asn Ser Glu Leu Thr Asp Ala Ala
        80                  85                  90

Tyr Thr Ala Ile Leu Asp Asp Asn Ser Gln Phe Gly Gln Ile Thr Pro
    95                  100                 105

Ala Asn Ser Met Lys Trp Asp Ala Thr Glu Pro Thr Arg Gly Thr Phe
110                 115                 120                 125

Thr Phe Ser Gly Gly Asp Gln Ile Ala Asn Leu Ala Lys Thr Asn Gly
                130                 135                 140

Met Leu Leu Arg Gly His Asn Cys Val Trp Tyr Asn Gln Leu Pro Ser
            145                 150                 155

Trp Val Ala Asn Gly Gln Phe Thr Ala Ala Asp Leu Thr Thr Val Ile
                160                 165                 170

Gln Thr His Cys Ser Thr Leu Val Ser His Tyr Lys Gly Gln Val Tyr
    175                 180                 185

Ser Trp Asp Val Val Asn Glu Pro Phe Asn Asp Gly Thr Trp Arg
190                 195                 200                 205

Ser Asp Val Phe Tyr Asn Thr Leu Gly Thr Ser Tyr Val Pro Ile Ala
                210                 215                 220

Leu Lys Ala Ala Arg Ala Ala Asp Pro Ser Ala Lys Leu Tyr Ile Asn
            225                 230                 235
```

Asp Tyr Asn Ile Glu Gln Thr Gly Ala Lys Ala Thr Ala Met Leu Asn
        240                 245                 250

Leu Val Lys Gln Leu Ile Ala Asp Gly Val Pro Ile Asp Gly Val Gly
    255                 260                 265

Phe Gln Cys His Phe Ile Val Gly Glu Val Pro Gly Ser Phe Gln Thr
270                 275                 280                 285

Val Leu Glu Gln Phe Thr Ala Leu Gly Leu Glu Val Ala Ile Thr Glu
            290                 295                 300

Leu Asp Ile Arg Thr Thr Thr Pro Ala Ser Gln Ser Ala Leu Ala Gln
                305                 310                 315

Gln Glu Lys Asp Tyr Gln Ser Val Ile Gln Ala Cys Met Asn Val Lys
            320                 325                 330

Gly Cys Val Gly Ala Thr Leu Trp Asp Phe Thr Asp Lys Tyr Ser Trp
        335                 340                 345

Val Pro Ser Thr Phe Ser Gly Gln Gly Ala Ala Cys Pro Trp Asp Gln
350                 355                 360                 365

Asn Leu Val Lys Lys Pro Ala Tyr Thr Gly Ile Val Asn Ala Leu Ser
                370                 375                 380

Ala

```
<210> SEQ ID NO 11
<211> LENGTH: 1676
<212> TYPE: DNA
<213> ORGANISM: Trametes versicolor
<220> FEATURE:
<221> NAME/KEY: CDS
<222> LOCATION: (1)..(79)
<220> FEATURE:
<221> NAME/KEY: sig_peptide
<222> LOCATION: (1)..(66)
<220> FEATURE:
<221> NAME/KEY: mat_peptide
<222> LOCATION: (67)..()
<220> FEATURE:
<221> NAME/KEY: Intron
<222> LOCATION: (80)..(139)
<220> FEATURE:
<221> NAME/KEY: CDS
<222> LOCATION: (140)..(174)
<220> FEATURE:
<221> NAME/KEY: Intron
<222> LOCATION: (175)..(204)
<220> FEATURE:
<221> NAME/KEY: CDS
<222> LOCATION: (205)..(522)
<220> FEATURE:
<221> NAME/KEY: Intron
<222> LOCATION: (523)..(585)
<220> FEATURE:
<221> NAME/KEY: CDS
<222> LOCATION: (586)..(592)
<220> FEATURE:
<221> NAME/KEY: Intron
<222> LOCATION: (593)..(649)
<220> FEATURE:
<221> NAME/KEY: CDS
<222> LOCATION: (650)..(739)
<220> FEATURE:
<221> NAME/KEY: Intron
<222> LOCATION: (740)..(798)
<220> FEATURE:
<221> NAME/KEY: CDS
<222> LOCATION: (799)..(1066)
<220> FEATURE:
<221> NAME/KEY: Intron
<222> LOCATION: (1067)..(1120)
<220> FEATURE:
<221> NAME/KEY: CDS
```

-continued

```
<222> LOCATION: (1121)..(1229)
<220> FEATURE:
<221> NAME/KEY: Intron
<222> LOCATION: (1230)..(1285)
<220> FEATURE:
<221> NAME/KEY: CDS
<222> LOCATION: (1286)..(1378)
<220> FEATURE:
<221> NAME/KEY: Intron
<222> LOCATION: (1379)..(1431)
<220> FEATURE:
<221> NAME/KEY: CDS
<222> LOCATION: (1432)..(1518)
<220> FEATURE:
<221> NAME/KEY: Intron
<222> LOCATION: (1519)..(1583)
<220> FEATURE:
<221> NAME/KEY: CDS
<222> LOCATION: (1584)..(1673)

<400> SEQUENCE: 11 atg aag ggc ctc gcc gca ctc gtc gca ctc gcc acc atc gtc gcc gtc         48
Met Lys Gly Leu Ala Ala Leu Val Ala Leu Ala Thr Ile Val Ala Val
-20              -15                 -10 ccg gcc aac gcc gtc gcg gtc tgg ggc caa t gtgagcatcc ctcacccgga         99
Pro Ala Asn Ala Val Ala Val Trp Gly Gln
         -5                  -1  1 cttatacctc tggaatagta acactgacat gcgtttgcag gc gga gta cgc acc         153
                                              Cys Gly Val Arg Thr
                                                    5 ttt gcc cgc tgc gct cgt cct gtctacgctt gacactgacc tctctgtcag ggt        207
Phe Ala Arg Cys Ala Arg Pro                                     Gly
10              15 atc ggc ttc agt gga tcg acc aca tgt gat gcc ggc acc aca tgc atc        255
Ile Gly Phe Ser Gly Ser Thr Thr Cys Asp Ala Gly Thr Thr Cys Ile
        20                  25                  30 gtg ctc aac tcc tac tac tcg cag tgc cag ccg ggt gcg agc gcg ccc        303
Val Leu Asn Ser Tyr Tyr Ser Gln Cys Gln Pro Gly Ala Ser Ala Pro
    35                  40                  45 gcg ccc acg aca tcc gcc ccc cag ccg ccc ccg acc aca ccg gct ggt        351
Ala Pro Thr Thr Ser Ala Pro Gln Pro Pro Pro Thr Thr Pro Ala Gly
50                  55                  60                  65 ggc tcg ccc gcg ccc gcg gcg acc gga ctc aac gct gcg ttc aag aag        399
Gly Ser Pro Ala Pro Ala Ala Thr Gly Leu Asn Ala Ala Phe Lys Lys
                70                  75                  80 cac ggc aag aag ttc tgg ggc acc gcg acg gac tca aac cgc ttc agc        447
His Gly Lys Lys Phe Trp Gly Thr Ala Thr Asp Ser Asn Arg Phe Ser
            85                  90                  95 aac ccg acg gac tcc gcg gtc acc gtc cgc gag ttc ggc cag gtc acg        495
Asn Pro Thr Asp Ser Ala Val Thr Val Arg Glu Phe Gly Gln Val Thr
        100                 105                 110 cct gag aac tcc atg aag tgg gat gcg gtgagtgcct actgggcgcg                542
Pro Glu Asn Ser Met Lys Trp Asp Ala
    115                 120 tcggcgtcga gtgagcatgt gcttatgatt attttcgtcg tag act gag c                592
                                              Thr Glu gtgcgtattt agtgaggctt cggatggtcc tcccaggaaa ctgacagcat gttgcag           649 ct tcc cgc aac cag ttc tcg ttc agc ggc tct gat gcg ctg gtc aac          696
Pro Ser Arg Asn Gln Phe Ser Phe Ser Gly Ser Asp Ala Leu Val Asn
125                 130                 135                 140 ttc gct acg acg aat ggc ctg ctc gtc cgc gct cac acc ctc g               739
Phe Ala Thr Thr Asn Gly Leu Leu Val Arg Ala His Thr Leu
                145                 150
```

```
gtaagcatgt tctcgttgtc tcatctctga agtggcgact aactgttctt ggggcgcag          798 tc  tgg cat tcg caa ctg ccg tcc tgg gtc tct gcg atc aac gac cgc          845
Val Trp His Ser Gln Leu Pro Ser Trp Val Ser Ala Ile Asn Asp Arg
155             160                 165                 170 gcg acg ctc acg tcc gtg atc cag aac cac atc gcg aac gtc gca ggc          893
Ala Thr Leu Thr Ser Val Ile Gln Asn His Ile Ala Asn Val Ala Gly
            175                 180                 185 cgg tac aag ggc aag gtg tac tcc tgg gac gtc gtg aac gag atc ttc          941
Arg Tyr Lys Gly Lys Val Tyr Ser Trp Asp Val Val Asn Glu Ile Phe
        190                 195                 200 aac gag gac ggc acg ttc cgc tcg tcg gtg ttt tca aac gtc ctc ggc          989
Asn Glu Asp Gly Thr Phe Arg Ser Ser Val Phe Ser Asn Val Leu Gly
    205                 210                 215 cag gac ttc gtc acg atc gcg ttc cag gcg gca cgg gcg gcg gac ccg          1037
Gln Asp Phe Val Thr Ile Ala Phe Gln Ala Ala Arg Ala Ala Asp Pro
220                 225                 230 aac gcg aag ctc tac atc aac gac tac aa  gtgtgtctcg cgggttggct            1086
Asn Ala Lys Leu Tyr Ile Asn Asp Tyr Asn
235                 240 tggtgtgcct ttgctgatgc gtttgtgtat gcag c  ctc gac acc gtg aac cca         1139
                                        Leu Asp Thr Val Asn Pro
                                            245                 250 aag ctc aac ggt gtt gtc aac ctt gtc aag aag atc aac ggc ggc ggc          1187
Lys Leu Asn Gly Val Val Asn Leu Val Lys Lys Ile Asn Gly Gly Gly
                255                 260                 265 acc aag ctg atc gac ggt atc ggt act cag gcc cac ctt tcg              1229
Thr Lys Leu Ile Asp Gly Ile Gly Thr Gln Ala His Leu Ser
            270                 275                 280 gtaagtgtat caggactatt tagcagactg acgtgctgac gctagagctc ggatag gct        1288
                                                              Ala ggc ggc gct ggc gga ttc cag gct gcg ctc acg cag ctg gct acc gcc         1336
Gly Gly Ala Gly Gly Phe Gln Ala Ala Leu Thr Gln Leu Ala Thr Ala
        285                 290                 295 ggc acg gag atc gct atc acg gag ctc gac att gcg ggt gcc                 1378
Gly Thr Glu Ile Ala Ile Thr Glu Leu Asp Ile Ala Gly Ala
300                 305                 310 gtaagtatcc gttacaatga tttcgcgctg ctccttattt atgtcgcatt cag gcc          1434
                                                            Ala ccc aat gac tac tcg acg ctg gtc aag gcg tgt ctc gcg gtg gag agc        1482
Pro Asn Asp Tyr Ser Thr Leu Val Lys Ala Cys Leu Ala Val Glu Ser
            315                 320                 325 tgc gtg tcc atc aca agc tgg gga gtc cgc gat ccc gtaagcaata             1528
Cys Val Ser Ile Thr Ser Trp Gly Val Arg Asp Pro
330                 335                 340 tatcttcctt gttgacggtg atgagacgtt ctcaccatgt gcatgctttt atcag gac       1586
                                                                Asp tcc tgg agg gcg tcc acc aac ccc ctc ttg ttc gac gcg aac ttc aac        1634
Ser Trp Arg Ala Ser Thr Asn Pro Leu Leu Phe Asp Ala Asn Phe Asn
        345                 350                 355 ccg aag ccc gca tac act gcg gtt atg cag gcc ctg gct tga                1676
Pro Lys Pro Ala Tyr Thr Ala Val Met Gln Ala Leu Ala
    360                 365                 370

<210> SEQ ID NO 12
<211> LENGTH: 392
<212> TYPE: PRT
<213> ORGANISM: Trametes versicolor
```

```
<400> SEQUENCE: 12

Met Lys Gly Leu Ala Ala Leu Val Ala Leu Ala Thr Ile Val Ala Val
-20                 -15                 -10

Pro Ala Asn Ala Val Ala Val Trp Gly Gln Cys Gly Val Arg Thr Phe
 -5              -1   1               5                       10

Ala Arg Cys Ala Arg Pro Gly Ile Gly Phe Ser Gly Ser Thr Thr Cys
                 15              20                  25

Asp Ala Gly Thr Thr Cys Ile Val Leu Asn Ser Tyr Tyr Ser Gln Cys
             30              35                  40

Gln Pro Gly Ala Ser Ala Pro Ala Pro Thr Thr Ser Ala Pro Gln Pro
             45              50              55

Pro Pro Thr Thr Pro Ala Gly Gly Ser Pro Ala Pro Ala Ala Thr Gly
 60              65              70

Leu Asn Ala Ala Phe Lys Lys His Gly Lys Lys Phe Trp Gly Thr Ala
 75              80              85                      90

Thr Asp Ser Asn Arg Phe Ser Asn Pro Thr Asp Ser Ala Val Thr Val
                 95              100                 105

Arg Glu Phe Gly Gln Val Thr Pro Glu Asn Ser Met Lys Trp Asp Ala
             110             115                 120

Thr Glu Pro Ser Arg Asn Gln Phe Ser Phe Ser Gly Ser Asp Ala Leu
             125             130                 135

Val Asn Phe Ala Thr Thr Asn Gly Leu Leu Val Arg Ala His Thr Leu
             140             145                 150

Val Trp His Ser Gln Leu Pro Ser Trp Val Ser Ala Ile Asn Asp Arg
155             160             165                 170

Ala Thr Leu Thr Ser Val Ile Gln Asn His Ile Ala Asn Val Ala Gly
                 175             180                 185

Arg Tyr Lys Gly Lys Val Tyr Ser Trp Asp Val Val Asn Glu Ile Phe
             190             195                 200

Asn Glu Asp Gly Thr Phe Arg Ser Ser Val Phe Ser Asn Val Leu Gly
             205             210                 215

Gln Asp Phe Val Thr Ile Ala Phe Gln Ala Ala Arg Ala Ala Asp Pro
220             225                 230

Asn Ala Lys Leu Tyr Ile Asn Asp Tyr Asn Leu Asp Thr Val Asn Pro
235             240             245                 250

Lys Leu Asn Gly Val Val Asn Leu Val Lys Lys Ile Asn Gly Gly Gly
                 255             260                 265

Thr Lys Leu Ile Asp Gly Ile Gly Thr Gln Ala His Leu Ser Ala Gly
             270             275                 280

Gly Ala Gly Gly Phe Gln Ala Ala Leu Thr Gln Leu Ala Thr Ala Gly
             285             290                 295

Thr Glu Ile Ala Ile Thr Glu Leu Asp Ile Ala Gly Ala Ala Pro Asn
300             305                 310

Asp Tyr Ser Thr Leu Val Lys Ala Cys Leu Ala Val Glu Ser Cys Val
315             320             325                 330

Ser Ile Thr Ser Trp Gly Val Arg Asp Pro Asp Ser Trp Arg Ala Ser
                 335             340                 345

Thr Asn Pro Leu Leu Phe Asp Ala Asn Phe Asn Pro Lys Pro Ala Tyr
             350             355                 360

Thr Ala Val Met Gln Ala Leu Ala
             365             370
```

POLYPEPTIDES HAVING XYLANASE ACTIVITY AND POLYNUCLEOTIDES ENCODING SAME

STATEMENT AS TO RIGHTS TO INVENTIONS MADE UNDER FEDERALLY SPONSORED RESEARCH AND DEVELOPMENT

This invention was made in part with Government support under Cooperative Agreement DE-FC36-08G018080 awarded by the Department of Energy. The government has certain rights in this invention.

CROSS-REFERENCE TO RELATED APPLICATION

This application claims priority or the benefit under 35 U.S.C. §119 of U.S. provisional application No. 61/531,422 filed on Sep. 6, 2011, the contents of which is fully incorporated herein by reference.

BACKGROUND OF THE INVENTION

1. Field of the Invention

The present invention relates to polypeptides having xylanase activity and polynucleotides encoding the polypeptides. The invention also relates to nucleic acid constructs, vectors, and host cells comprising the polynucleotides as well as methods of producing and using the polypeptides.

2. Description of the Related Art

Cellulose is a polymer of glucose linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol. Xylanases degrade beta-1,4-xylan into xylose, thus breaking down hemicellulose, one of the major components of plant cell walls.

There is a need in the art to improve cellulolytic and hemicellulolytic enzyme compositions through supplementation with additional enzymes to increase efficiency and to provide cost-effective enzyme solutions for degradation of lignocellulose.

The present invention provides polypeptides having xylanase activity and polynucleotides encoding the polypeptides.

SUMMARY OF THE INVENTION

The present invention relates to isolated polypeptides having xylanase activity selected from the group consisting of:

(a) a polypeptide having at least 67% sequence identity to the mature polypeptide of SEQ ID NO: 2, or a polypeptide having at least 61% sequence identity to the mature polypeptide of SEQ ID NO: 4, or a polypeptide having at least 61% sequence identity to the mature polypeptide of SEQ ID NO: 6, or a polypeptide having at least 90% sequence identity to the mature polypeptide of SEQ ID NO: 8, or a polypeptide having at least 79% sequence identity to the mature polypeptide of SEQ ID NO: 10, or a polypeptide having at least 92% sequence identity to the mature polypeptide of SEQ ID NO: 12;

(b) a polypeptide encoded by a polynucleotide that hybridizes under low, or medium, or medium-high, or high, or very high stringency conditions with (i) the mature polypeptide coding sequence of SEQ ID NO: 1, SEQ ID NO: 3, SEQ ID NO: 5, SEQ ID NO: 7, SEQ ID NO: 9, or SEQ ID NO: 11, (ii) the cDNA sequence thereof, or (iii) the full-length complement of (i) or (ii);

(c) a polypeptide encoded by a polynucleotide having at least 60% sequence identity to the mature polypeptide coding sequence of SEQ ID NO: 1, SEQ ID NO: 3, SEQ ID NO: 5, SEQ ID NO: 7, SEQ ID NO: 9, or SEQ ID NO: 11; or the cDNA sequence thereof;

(d) a variant of the mature polypeptide of SEQ ID NO: 2, SEQ ID NO: 4, SEQ ID NO: 6, SEQ ID NO: 8, SEQ ID NO: 10, or SEQ ID NO: 12 comprising a substitution, deletion, and/or insertion at one or more (e.g., several) positions; and (e) a fragment of the polypeptide of (a), (b), (c), or (d) that has xylanase activity.

The present invention also relates to isolated polypeptides comprising a catalytic domain selected from the group consisting of:

(a) a catalytic domain having at least 60% sequence identity to the catalytic domain of SEQ ID NO: 2 (for example, amino acids 19 to 352 of SEQ ID NO: 2), a catalytic domain having at least 60% sequence identity to the catalytic domain of SEQ ID NO: 4 (for example, amino acids 21 to 351 of SEQ ID NO: 4), a catalytic domain having at least 60% sequence identity to the catalytic domain of SEQ ID NO: 6 (for example, amino acids 24 to 342 of SEQ ID NO: 6), a catalytic domain having at least 60% sequence identity to the catalytic domain of SEQ ID NO: 8 (for example, amino acids 82 to 395 of SEQ ID NO: 8), a catalytic domain having at least 60% sequence identity to the catalytic domain of SEQ ID NO: 10 (for example, amino acids 87 to 401 of SEQ ID NO: 10), or a catalytic domain having at least 60% sequence identity to the catalytic domain of SEQ ID NO: 12 (for example, amino acids 97 to 392 of SEQ ID NO: 12);

(b) a catalytic domain encoded by a polynucleotide having at least 60% sequence identity to the catalytic domain coding sequence of SEQ ID NO: 1 (for example, nucleotides 55-1515 of SEQ ID NO: 1), a catalytic domain encoded by a polynucleotide having at least 60% sequence identity to the catalytic domain coding sequence of SEQ ID NO: 3 (for example, nucleotides 61-249, 307-524, 649-665, 721-867, 930-1237, 1295-1351, and 1405-1461 of SEQ ID NO: 3), a catalytic domain encoded by a polynucleotide having at least 60% sequence identity to the catalytic domain coding sequence of SEQ ID NO: 5 (for example, nucleotides 79-273, 325-430, 472-598, 718-734, 789-935, 990-1297, and 1353-1400 of SEQ ID NO: 5), a catalytic domain encoded by a polynucleotide having at least 60% sequence identity to the catalytic domain coding sequence of SEQ ID NO: 7 (for example, nucleotides 310-453, 511-728, 786-787, 845-865, 923-1069, 1137-1441, 1503-1559, and 1618-1665 of SEQ ID NO: 7), a catalytic domain encoded by a polynucleotide having at least 60% sequence identity to the catalytic domain coding sequence of SEQ ID NO: 9 (for example, nucleotides 316-459, 526-743, 799-800, 859-879, 936-1082, 1143-1447, and 1507-1614 of SEQ ID NO: 9), or a catalytic domain encoded by a polynucleotide having at least 60% sequence identity to the catalytic domain coding sequence of SEQ ID NO: 11 (for example, nucleotides 379-522, 586-592, 650-739, 799-1066, 1121-1229, 1286-1378, 1432-1518, and 1584-1673 of SEQ ID NO: 11);

(c) a variant of a catalytic domain comprising a substitution, deletion, and/or insertion of one or more (several) amino acids of the catalytic domain of SEQ ID NO: 2, SEQ ID NO: 4, SEQ ID NO: 6, SEQ ID NO: 8, SEQ ID NO: 10, or SEQ ID NO: 12; and (d) a fragment of a catalytic domain of (a), (b), or (c), which has xylanase activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to processes for degrading a cellulosic material or xylan-containing material, comprising: treating the cellulosic material or xylan-containing material with an enzyme composition in the presence of a polypeptide having xylanase activity of the present invention. In one aspect, the processes further comprise recovering the degraded or converted cellulosic material or xylan-containing material.

The present invention also relates to processes of producing a fermentation product, comprising: (a) saccharifying a cellulosic material or xylan-containing material with an enzyme composition in the presence of a polypeptide having xylanase activity of the present invention; (b) fermenting the saccharified cellulosic material or xylan-containing material with one or more (e.g., several) fermenting microorganisms to produce the fermentation product; and (c) recovering the fermentation product from the fermentation.

The present invention also relates to processes of fermenting a cellulosic material or xylan-containing material, comprising: fermenting the cellulosic material or xylan-containing material with one or more (e.g., several) fermenting microorganisms, wherein the cellulosic material or xylan-containing material is saccharified with an enzyme composition in the presence of a polypeptide having xylanase activity of the present invention. In one aspect, the fermenting of the cellulosic material or xylan-containing material produces a fermentation product. In another aspect, the processes further comprise recovering the fermentation product from the fermentation.

The present invention also relates to a polynucleotide encoding a signal peptide comprising or consisting of amino acids 1 to 18 of SEQ ID NO: 2, amino acids 1 to 20 of SEQ ID NO: 4, amino acids 1 to 23 of SEQ ID NO: 6, amino acids 1 to 19 of SEQ ID NO: 8, amino acids 1 to 19 of SEQ ID NO: 10, or amino acids 1 to 22 of SEQ ID NO: 12, which is operably linked to a gene encoding a protein; nucleic acid constructs, expression vectors, and recombinant host cells comprising the polynucleotides; and methods of producing a protein.

SEQUENCES OF THE INVENTION

*Trametes versicolor* Strain NN055586 Genomic Nucleotide Sequence (SEQ ID NO: 1):

```
   1 ATGCACTTCT CACTCCTCGC AGCCTTCATC GCGCTGGCTC CGGCCGCGCT CGCGATCCCC GCGACCCCCG TGGTCGATGC

81 GAGTCTCCCC GGCTCGACCG CGAACGTGGC GGGTCTGCAC GCCGTCGCGA AGGCGGCGGG CAAGCTCTAC TTGGGCACTG

161 CGACGGACAA TAACGAGCTT ACCAACACGC AGTACACCGC CATCCTCGAG GCTCCGAACA TGTTCGGCCA GATCACCGCC

241 GAGAACACCA TGAAATGGGT CAGTTGCGCC TTGTCGCGAT GTTCCGAGCA CGTTCCGCAA GCTAACGATT TGATGCTAGG

321 ACGCGACCGA GCCCCAGCAG AACGTGTTCA CGTTCACGCA GGGCGACCAG ATCGCGAACC TGGCGAAGTC CCACGGGATG

401 CTGCTGCGCG GTAACGACAG TCTTGAAGGG GCCGAAAATG TGGAAGAACT GAATGTTTTC GCAGGTCACA ACTGCGTCTG

481 GCACCAACAG CTCCCGAGCT GGGTAACTGC CGGGAACTTC AATGCACAGC AGCTTACGCA GATCATCCAA AACCACTGCG

561 GCACGGTCGT CGGACACTAC AAGGGACAAG TGTGAGTGTT GGCCATATCC GCCGACGTGT ATCGTGTGCT GACCGTGTTT

641 TATAGTTGTA CGTGACGCTT GTTGCTTGAT CGTATGAATC CACTTAGCTG ACTCGACGCA GTGAGCTGGG ATGTAGTAAA

721 CGGTAACGGA CATTCCTTCT CTTTGCTACA CACAACTCGG ACTCACACTC GGCTGCAGAG CCTCTCAACG ACGACGGCTC

801 GTTCCGCCAG GACGTGTTCT TCAACACTCT CGGCTCGGGC TACATCGCGA CGGCGCTCCG CGCTGCCAGG GCCGCAGACC

881 CTGCGGCGAA GCTGTACATC AACGAGTTTA ACGTCGAGGG CCTAGGTTCG TCCCACCGTA TCCCCGCTCA TTGCATCGTC

961 TGAGCCCGAA TCTTCTAGGC GCAAAGTCGA CCGCCTTGAA GAACCTCGTC ACTTCGCTGA AGCAGCAGGG CGTCCCGATC

1041 GACGGCGTCG GTTTCCAGTG CCACTTCATC GTCGGCCAGG TCCCCACGAC GCTCATCCAG AGCATGCAGC AGTTCACTGC

1121 GCTCGGCCTC GAGGTGGCCA TCACGGAGCT CGACATCCGC ATGACGCTCC CTGAAACTGC GGCGCTGCTC GAGCAGCAGA

1201 AGCAGGACTT CCAGACTGTT ATCCACGCGT GTAAGTCCGT GGCGGGCTGT GTCGGCGTCA CTGTGTGGGA CTTCACCGAT

1281 AAGGTATGTC GTTGTCCCGC CCCGGCGAGA TGGTTGGATT AGCGTGCTCA CCGGTATTAT ACCAGTTCTC CTTCGTGCCG

1361 AGCACGTTCC CGGGTCAGGG TGCTGCCACT CCTTGGGATC AGGTACGTCC CGCCGAACCT TGGGCCTTAC AAGCTCCGGG

1441 AGAGGGCTAA CTGCGGATGC GCAGAACCTG GTGAAGAAGC CGGCATTTGA TGGCATCGTC GCCGGATTCC AGCAGTGA
```

Exons/Introns (in base pairs) of SEQ ID NO: 1:

| Exon 1 | 1-258 bp |
| --- | --- |
| Intron 1 | 259-319 bp |
| Exon 2 | 320-410 bp |
| Intron 2 | 411-464 bp |
| Exon 3 | 465-591 bp |
| Intron 3 | 592-645 bp |
| Exon 4 | 646-651 bp |
| Intron 4 | 652-701 bp |
| Exon 5 | 702-715 bp |
| Intron 5 | 716-778 bp |
| Exon 6 | 779-925 bp |
| Intron 6 | 926-978 bp |
| Exon 7 | 979-1283 bp |
| Intron 7 | 1284-1345 bp |
| Exon 8 | 1346-1402 bp |
| Intron 8 | 1403-1464 bp |
| Exon 9 | 1465-1518 bp |

Features (in base pairs) of SEQ ID NO: 1:

| Signal Peptide | 1-54 bp |
| --- | --- |
| Xylanase catalytic site | 55-1515 bp |
| Stop codon | 1516-1518 bp |

Protein Sequence of *Trametes versicolor* Strain NN055586 protein (SEQ ID NO: 2):

```
  1 MHFSLLAAFI ALAPAALAIP ATPVVDASLP GSTANVAGLH AVAKAAGKLY LGTATDNNEL
 61 TNTQYTAILE APNMFGQITA ENTMKWDATE PQQNVFTFTQ GDQIANLAKS HGMLLRGHNC
121 VWHQQLPSWV TAGNFNAQQL TQIIQNHCGT VVGHYKGQVC TELGCKPLND DGSFRQDVFF
181 NTLGSGYIAT ALRAARAADP AAKLYINEFN VEGLGAKSTA LKNLVTSLKQ QGVPIDGVGF
241 QCHFIVGQVP TTLIQSMQQF TALGLEVAIT ELDIRMTLPE TAALLEQQKQ DFQTVIHACK
301 SVAGCVGVTV WDFTDKFSFV PSTFPGQGAA TPWDQNLVKK PAFDGIVAGF QQ
```

Features of SEQ ID NO: 2 (amino acid positions):

| Signal Peptide | 1-18 |
| --- | --- |
| Xylanase catalytic site | 19-352 |

Signal Peptide Sequence of SEQ ID NO: 2:

```
MHFSLLAAFIALAPAALA
```

*Trametes versicolor* Strain NN055586 Genomic Nucleotide Sequence (SEQ ID NO: 3):

```
  1 ATGCTCTCTC TGTCAAAAAG CCTTCTTGCG CTCTCTGTCT TGGTCCGAGG TGCGCTCGCC GTACCTGCCA GCGATGCGAG
 81 TAGCGCTCTG TTCCCATTGT CGGGGCTGAA TCTGGCCGCC AAGGGCGCGC GGAAGTTGTA CCTTGGCACG GCAACGAACA
161 GCGAGCAGTG GAACGACACG ACGTACTTCA ACATCCTGAA GAACAACGCC GAGTTCGGGC AGGTAACGCC CGCGAACGTC
241 ATGAAATGGG TACGTTGTCG GCGTCCTCTT CGTACTGACG ATGTTGAGGC TAACTTTGAC GCATAGTTTG CGACGGAGCC
321 TGAGGAGGGC GTCTTCACGT TCCAGGACGG GGATATCATC GCGGACTTTA CCAAAAAGAC GGGGAAGCTG CTGCGCGGAC
401 ACAACTGCGT GTGGCACAAC CAGCTCCCCG ACTGGCTAGA AACCGGCACG TTCAGTGCGC CCGAGCTCGC ATTCATTGTC
481 TCGCGGCACT GCTTCAACCT CGTGAACCAC TACCAAGGCT ATGTGTGAGT GCAATTCGTT ACCTGTGATC CTGCTCAACG
561 ATCTAAATCG GTACACGGCA GGTGTACGTA CAAGCGTGTC GGTGATGTTT CATTGAGGCT GATGGCTTAT TTTGGAAAAT
641 TCAGATAGCT GGGACGTCAT CAATGGTTCG TGCTACTTGA CTTCCCGGAT GTGCTTGTTT CCGATCTCGA ATTTTGCTAG
721 AGGCTTTCAA CGACGACGGA ACCTTCCGTT CGGATATCTT CTTCGACACG CTCAACACAA CCTACATCCC GCTCGCCCTC
801 TACGCAGCAC GCGCCGCGGA CCCCAAAGCG AAGCTCTACA TCAACGACTT CAACATCGAA GGCATAGGTA CGCCACATAA
881 CACCATCTGC CCGCCGCAAA GCCCTGCCAC CCAACTACCC TACTCGCAGG TGCGAAGTCC GACGCGCTCA AGAGTCTCAT
961 CAAGGAGCTC AAGAGCCAAA ACGTCCCCAT CGACGGCGTC GGGCTGCAGT CGCACTTCGA GGTCGGCGGC GTCCCGCCCA
```

```
1041 CGCTGCAGCA GAACATGGAG GAGTTCGTCG CGCTCGGGCT CGAGGTCGCG ATCACGGAGC TCGACATCCG CTTCACCGCG

1121 CTCCCGCCGA CGCCTGCAGG CCTCGCGCAG CAGAAGGCGG ACTACGAGAC CGTCGTCGCC GCGTGCAACG CGGTCCCGAA

1201 GTGCGTCGGG GTCACGCTGT GGGACTTCAC GGACAAGGTG CGTCTGCGAG ATTGTGGTCG TGTGATGGGT GTTGATGCCG

1281 GATGGGCGGG GTAGTACTCG TGGATCCCGG GGACCTTCCC TGGGCAGGGA GATGCGTGTC CCTGGACGGA TGTACGTTCC

1361 TTAGTCTGTC TCGTCCGAAG GTGTGATCTA ATGATGTACC ACAGGAATTT GTGAAGAGGC CAGCATACGA GGGCATCATC

1441 GAGGGGTTCA AGGCCCACCA TTAG
```

Exons/Introns (in base pairs) of SEQ ID NO: 3:

| | |
|---|---|
| Exon 1 | 1-249 bp |
| Intron 1 | 250-306 bp |
| Exon 2 | 307-524 bp |
| Intron 2 | 525-648 bp |
| Exon 3 | 649-665 bp |
| Intron 3 | 666-720 bp |
| Exon 4 | 721-867 bp |
| Intron 4 | 868-929 bp |
| Exon 5 | 930-1237 bp |
| Intron 5 | 1238-1294 bp |
| Exon 6 | 1295-1351 bp |

-continued

| | |
|---|---|
| Intron 6 | 1352-1404 bp |
| Exon 7 | 1405-1464 bp |

Features (in base pairs) of SEQ ID NO: 3:

| | |
|---|---|
| Signal Peptide | 1-60 bp |
| Xylanase catalytic site | 61-249, 307-524, 649-665, 721-867, 930-1237, 1295-1351, 1405-1461 bp |
| Stop codon | 1462-1464 bp |

Protein Sequence of *Trametes versicolor* Strain NN055586 protein (SEQ ID NO: 4):

```
  1 MLSLSKSLLA LSVLVRGALA VPASDASSAL FPLSGLNLAA KGARKLYLGT ATNSEQWNDT
 61 TYFNILKNNA EFGQVTPANV MKWFATEPEE GVFTFQDGDI IADFTKKTGK LLRGHNCVWH
121 NQLPDWLETG TFSAPELAFI VSRHCFNLVN HYQGYVWDVI NEAFNDDGTF RSDIFFDTLN
181 TTYIPLALYA ARAADPKAKL YINDFNIEGI GAKSDALKSL IKELKSQNVP IDGVGLQSHF
241 EVGGVPPTLQ QNMEEFVALG LEVAITELDI RFTALPPTPA GLAQQKADYE TVVAACNAVP
301 KCVGVTLWDF TDKYSWIPGT FPGQGDACPW TDEFVKRPAY EGIIEGFKAH H
```

Features of SEQ ID NO: 4 (amino acid positions):

| | |
|---|---|
| Signal Peptide | 1-20 |
| Xylanase catalytic site | 21-351 |

Signal Peptide Sequence of SEQ ID NO: 4:

MLSLSKSLLALSVLVRGALA

*Trametes versicolor* Strain NN055586 Genomic Nucleotide Sequence (SEQ ID NO: 5):

```
  1 ATGATGACGA ACTTCCACCT AGTCTCCTCG TTGATCGCGC TCGCGTTTCT TTCGCTGACC GGCTTAGCAT CCATTCCGTC
 81 GACACGCGCT CTGGCTGGAA ATTCCTCGAG GATCAATTCT CCTTCTGGCT TGAACTTGGC GGCTTTGGAA GCCCGGAAGC
161 TGTACTTTGG TACTGCGACC AACAACGTCG AGCTCAACGA CACGGCATAC TTCGACATTC TCGATGATTT CAAAATGTTC
241 GGTCAAATTA CGCCCGCCAA AGGCATGAAA TGGGTCCGTT CTCCAACTTC TGCATCATAA ATCGCTCGCT GATTGTTTTG
321 GAAGATGGAG ACGGAACCTG AGCGAGGCGT TTTCACCTTC GCGCAGGCAG ACCAAATCGC GCAACTTGCC AGCGAGGGCG
401 GAAAGCTGTT GAGAGGCTCG TACTCGAAAG GTCCCTCGCT ACCCCATACG TGCTAACATT CCGTTCTGCA GGCCACAACT
481 GCGTATGGTA TAATGCGCTT CCCGGGTGGG TCACAAATAC CACGTGGACG GCCTCCGAGA TGGCCGAGGT CGTACAGGAG
561 CATTGTTTCA ACATCGTCCG TTACTGGCAA GGACAAGCGT GAGTACCGAT CTCTCTCATT AATATCGTGT CTCTCAATTT
```

```
 641 TTATTCCGAG TAGATGTGAG TATCAACGCC TTCCGGAGGA ATCCCGCTGA ACATAGGCCG TCCTTTTACA CAGACAGCTG

721 GGACGTTATT AACGGTGAGT TGCTCGAGAT TGAAGGCAGC TGCCCGTAGC TTACACCATT TCCCGCAGAG CCATTCAACG

801 ATGACGGAAC GTGGCGCGAG ACCATGTGGT TTAATACTCT CAACACGAGC TACATTCCGC TCGCGTTGCA CGCTGCGCGC

881 GCGGCCGATC CTCATACTAA GCTGTACATC AATGAGTACA ATATCACCGG AACAGGTGCG TCGTACGCCT CACGCTCAGA

961 CTATGCCTCC TTCATCATTC AGTATACAGG CCCGAAGGCG ACGTCCATGA AGAACCTCAT CAAAGACTTG AAGCGCGCTG

1041 GTGTGCCCGT TCACGGCGTT GGAGTTCAAG CGCACGAGAC CGTCGGGGAA GTTCCGACCG ACATCCGCAA GAACCTCGGG

1121 GAGTTCGTCG CACTCGGCGT CGAGGTCGCG ATCACAGAAC TCGACATCAA GTTCAACACG CTTCCTCCTG ATGCAGCCGG

1201 GCTCAAACAA CAGAAGCGAG ATTACGAAGC TATTGTCTCG GCGTGCGCGG AGGTAAAAGG ATGTGTGGGC GTGACGGTTT

1281 GGGACTTCAC GGACAAGGTG GGAAAGTATT CGACTTCACG AAGCAATACC AAGTATTCAC CTTTGCGTAC AGTACTCATG

1361 GATCCCCGGA ACGTTCCCTG GAACCGGCGA TGCTTGTCCT TGAgacgatg tgagcgtgat gctattgcgt attgcttttt 1441 ctactgactg tctctcgtac ttctttgtct caggatttgc acaagaagcc ggcgtactat ggaattttgg acgggtttgg 1521 gagatctcgc tga
```

Exons/Introns (in base pairs) of SEQ ID NO: 5:

| | |
|---|---|
| Exon 1 | 1-273 bp |
| Intron 1 | 274-324 bp |
| Exon 2 | 325-430 bp |
| Intron 2 | 431-471 bp |
| Exon 3 | 472-598 bp |
| Intron 3 | 599-717 bp |
| Exon 4 | 718-734 bp |
| Intron 4 | 735-788 bp |
| Exon 5 | 789-935 bp |
| Intron 5 | 936-989 bp |
| Exon 6 | 990-1297 bp |
| Intron 6 | 1298-1352 bp |
| Exon 7 | 1353-1403 bp |
| 3' UTR | 1404-1533 bp |

Features (in base pairs) of SEQ ID NO: 5:

| | |
|---|---|
| Signal Peptide | 1-69 bp |
| Xylanase catalytic site | 79-273, 325-430, 472-598, 718-734, 789-935, 990-1297, 1353-1400 bp |
| Stop codon | 1401-1403 bp |

Protein Sequence of *Trametes versicolor* Strain NN055586 protein (SEQ ID NO: 6):

```
  1 MMTNFHLVSS LIALAFLSLT GLASIPSTRA LAGNSSRINS PSGLNLAALE ARKLYFGTAT

61 NNVELNDTAY FDILDDFKMF GQITPAKGMK WMETEPERGV FTFAQADQIA QLASEGGKLL

121 RGSYSKGHNC VWYNALPGWV TNTTWTASEM AEVVQEHCFN IVRYWQGQAW DVINEPFNDD

181 GTWRETMWFN TLNTSYIPLA LHAARAADPH TKLYINEYNI TGTGPKATSM KNLIKDLKRA

241 GVPVHGVGVQ AHETVGEVPT DIRKNLGEFV ALGVEVAITE LDIKFNTLPP DAAGLKQQKR

301 DYEAIVSACA EVKGCVGVTV WDFTDKYSWI PGTFPGTGDA CP
```

Features of SEQ ID NO: 6 (amino acid positions):

| | |
|---|---|
| Signal Peptide | 1-23 |
| Xylanase catalytic site | 24-342 |

Signal Peptide Sequence of SEQ ID NO: 8:

```
MMTNFHLVSSLIALAFLSLTGLA
```

*Trametes versicolor* Strain NN055586 Genomic Nucleotide Sequence (SEQ ID NO: 7):

```
 1 ATGAACCTCT CAGCGTCGTT CGCAGTACTT GTCGCTCTGA TCCCGTACGC CCTCGCGCAG TCCCCGGAGT GGGGCCAATG

81 CGGCGGAACA GGCTATACGG GCGCCACGAC TTGCGTGTCC GGAACGGTAT GCACGGTGAT CAACCCGTAC TACTCACAAT
```

```
                                          -continued
161 GTCTCGCAGG CACTGTAAGT ACACGACACA CGCATCTTTG TCAGGTCACA GGGGAGCCAA ACGCTGACGG TCACCTCAAG 241 GCCACATCCG CGCTCCTCGC TCCCAGCCCA ACTGTGAGCA CCGGCGCACC CGCCCCGAGC GTCAGCGGTC TGCACACTCT 321 CGCCAAAGCC GCTGGGAAGC TCTACTTTGG CAGCGCGACG GACAACCCCG AGCTGACCGA CACCGCCTAC GTCGCGAAGC 401 TCAGCGACAA CGCCGAGTTC GGCCAGATCA CCCCCGGTAA CAGCATGAAA TGGGTGAGTA CCGCACCCTC CATCCCCATT 481 CTCAGGTTTG TGAGAATGAA TGCGTCGTAG GACGCGACGG AGCCGACGCG GGGGACGTTC ACGTTCACGG GCGGGGACGT 561 GGTTGCGAGC CTGGCGGAGA AGAACGGGCA GCTGCTGCGC GGGCACAACT GCGTGTGGTA CAACCAGCTC CCGAGCTGGG 641 TCGCGAACGG GCAGTTCACG GCTGCGGATT TGACGGACGT GATCACGACG CACTGCGGCA CGCTCGTTGG CCACTACAAG 721 GGACAAATGT GAGTGCCGGT CTTACTCTCG AATAATCGTG TTACAGTATG CTAATGGAGG CGCAGCTGTA CGCATCATAG 801 GGTTGTTCGT GACTGTTGCT GGTACTGACT TGCTCGTACC GAAGACTCTT GGGACGTCAT CAATGGTCAG TTGTCGTGAG 881 CGAGATCGTG CATTACAGTA TGCTCAATAT TTTCGTGCCT AGAACCCTTT AACGACGACG GTACCTGGCC CTCGGATGTG 961 TTCTTCAATA CGCTCGGTCA GTCCTACGTC TCCATCGCGC TCAAAGCCGC ACGCGCTGCA GACCCCAACG CCAAGCTCTA 1041 CATCAACGAC TACAACATCG AGCAGACCGG TGCGCCCCTC CTTTCCTTGA TACTTCCCTT AGCACCATCA AACTAACCCT 1121 GCATATGATC GCACAGGCGC GAAGTCGACC GCGATGCTGA ACCTCGTGAA GCAGCTACAA GCAGACGGCG TGCCAATCGA 1201 CGGCGTCGGC TTCCAGAGCC ACTTCATCGT TGGCGAGGTC CCCGGCTCGT TCCAGACCGT GCTCGAGCAG TTCACCGCGC 1281 TCGGGCTCGA GGTCGCGATC ACGGAGCTCG ACATCCGCAT GACGCTCCCC GCGACGGACG CGCTCCTCGC GCAGCAGCAG 1361 AAGGACTACC AGAGCGTCGT GCAGGCGTGC ATGAACGTGC AGGGCTGTGT GGGCGTCACG ATCTGGGACT GGACGGACAA 1441 GGTGCGTGTG GTGGGGTGGA GAGAGCGAGC GAGGAGGGTG CTGATAGGGA CTCTTGGGGC AGTACTCGTG GGTGCCGTCG 1521 ACGTTCTCGG GACAGGGCGC GGCTCTGCCT TGGGACGAGG TTGCGTGTCC TCTCCCGCGT TCTGGGGATA CTCAATGGAC 1601 GCATTTACGT TCGTCAGACC TTCAACAAAA AGCCCGCATA CAGCGGCATC ACGGCGGCAC TGACGTGA
```

Exons/Introns (in base pairs) of SEQ ID NO: 7:

| | |
|---|---|
| Exon 1 | 1-174 bp |
| Intron 1 | 175-240 bp |
| Exon 2 | 241-453 bp |
| Intron 2 | 454-510 bp |
| Exon 3 | 511-728 bp |
| Intron 3 | 729-785 bp |
| Exon 4 | 786-787 bp |
| Intron 4 | 788-844 bp |
| Exon 5 | 845-865 bp |
| Intron 5 | 866-922 bp |
| Exon 6 | 923-1069 bp |
| Intron 6 | 1070-1136 bp |
| Exon 7 | 1137-1441 bp |
| Intron 7 | 1442-1502 bp |
| Exon 8 | 1503-1559 bp |
| Intron 8 | 1560-1617 bp |
| Exon 9 | 1618-1668 bp |

Features (in base pairs) of SEQ ID NO: 7:

| | |
|---|---|
| Signal Peptide | 1-57 bp |
| Cellulose Binding Module 1 (CBM 1) | 58-168 bp |
| Linker | 169-174, 241-309 bp |
| Xylanase catalytic site | 310-453, 511-728, 786-787, 845-865, 923-1069, 1137-1441, 1503-1559, 1618-1665 bp |
| Stop codon | 1666-1668 bp |

Protein Sequence of *Trametes versicolor* Strain NN055586 protein (SEQ ID NO: 8):

```
  1 MNLSASFAVL VALIPYALAQ SPEWGQCGGT GYTGATTCVS GTVCTVINPY YSQCLAGTAT

61 SAPSAPSPTV STGAPAPSVS GLHTLAKAAG KLYFGSATDN PELTDTAYVA KLSDNAEFGQ

121 ITPGNSMKWD ATEPTRGTFT FTGGDVVASL AEKNGQLLRG HNCVWYNQLP SWVANGQFTA

181 ADLTDVITTH CGTLVGHYKG QIYSWDVINE PFNDDGTWRS DVFFNTLGQS YVSIALKAAR

241 AADPNAKLYI NDYNIEQTGA KSTAMLNLVK QLQADGVPID GVGFQSHFIV GEVPGSFQTV

301 LEQFTALGLE VAITELDIRM TLPATDALLA QQQKDYQSVV QACMNVQGCV GVTIWDWTDK

361 YSWVPSTFSG QGAALPWDET FNKKPAYSGI TAALT
```

Features of SEQ ID NO: 8 (amino acid positions):

| | |
|---|---|
| Signal Peptide | 1-19 |
| Cellulose Binding Module 1 (CBM 1) | 20-56 |
| Linker | 57-81 |
| Xylanase catalytic site | 82-395 |

Signal Peptide Sequence of SEQ ID NO: 8:

MNLSASFAVLVALIPYALA

*Trametes versicolor* Strain NN055586 Genomic Nucleotide Sequence (SEQ ID NO: 9):

```
   1 ATGCAGCTCT CGACGACCTT CACCCTCCTC GCCGCGATCA TTCCGTTCGC CCTCGGGCAG GCCGCGGAGT GGGGCCAGTG

81 CGGTGGCATT GGCTGGACCG GCGCGACGAC GTGCGTGGCG GCACCACCT GCACGGTCAT GAACGCGTAC TACTCCCAGT

161 GCCTCCCCGG TTCTGTGAGT GGCTGTGCTG TGGTAGAGAC GTTCAACATG CTGACCGGTG AATGCTTGTA GGCTGCGCCC

241 GCGCCGACGA CGACCCCCAC CTCGCCTTCG AGCCCGGCGA CCCCGCCGTC CGCGCCTGCG CCAACCGGCA GCGGCCTCAA

321 CAAGCTCGCG AAGGCGGCTG GCAAGCTCTA CCTCGGCACT GCGACGGACA CAGCGAGCT CACCGATGCG GCGTACACCG

401 CCATCCTCGA CGACAACTCC CAGTTCGGCC AGATCACGCC CGCCAACAGC ATGAAATGGG TGCGCATTAT CCCTGCATCG

481 TGTACTAGAA CGCTCCTTGC TTATTGTTGT AAAATTGGAA TGCAGGACGC GACAGAGCCG ACTCGCGGAA CGTTCACGTT

561 CTCGGGTGGT GACCAGATCG CGAACCTGGC GAAGACGAAC GGGATGCTTC TCCGTGGACA CAACTGCGTG TGGTACAACC

641 AGCTCCCGAG CTGGGTTGCG AACGGCCAGT TCACCGCCGC GGACCTCACG ACCGTCATCC AGACGCACTG CAGCACCCTC

721 GTCAGCCACT ACAAGGGTCA AGTGTACGTG ATTCCTTCTG TGTATCTACT CTCCCAATAC TGACCCCATT TTCCGCAGTT

801 GTACGTCTAC GTTCGCATTT ATGATTCTTG TATGCATACT GACCGACATG ACAAAAAGAC TCCTGGGACG TCGTCAACGG

881 TTAGTGGTAT TACTCCACAA GTTCACCAGG GAAGTGTTCT GACAGTGATC TCCAGAGCCG TTCAACGACG ATGGTACCTG

961 GCGCTCGGAC GTGTTCTACA ACACGCTCGG CACTTCGTAC GTGCCCATCG CGCTCAAGGC TGCGCGCGCT GCGGACCCTA

1041 GCGCCAAACT CTACATCAAC GACTACAACA TTGAGCAGAC GGGTAGGTCC CCAGCATCCA TCTCCCAGGA GTGACGCCGC

1121 TCACGGCACA CACGCACCAC AGGCGCCAAG GCGACCGCGA TGCTGAACCT CGTGAAGCAG CTCATCGCCG ACGGCGTTCC

1201 GATCGACGGT GTCGGCTTCC AGTGCCACTT TATCGTTGGC GAGGTCCCCG GCTCGTTCCA GACCGTGCTC GAGCAGTTCA

1281 CCGCGCTCGG GCTCGAGGTC GCGATCACGG AGCTCGACAT CCGCACGACG ACGCCCGCGT CGCAGTCCGC GCTCGCACAG

1361 CAGGAGAAGG ACTACCAGTC GGTTATCCAG GCGTGCATGA ACGTCAAGGG CTGCGTTGGT GCCACCCTCT GGGACTTCAC

1441 CGACAAGGTT CGTAGGCAAG CTTTCTACGC GTGTAAGACG AATTGGCTGA CGCTCTTGCG ATGCAGTACT CCTGGGTCCC

1521 CTCGACGTTC TCCGGCCAAG GTGCGGCGTG CCCTTGGGAC CAGAACCTCG TCAAGAAGCC CGCGTACACT GGTATCGTCA

1601 ACGCTCTCAG CGCGTGA
```

Exons/Introns (in base pairs) of SEQ ID NO: 9:

| | |
|---|---|
| Exon 1 | 1-174 bp |
| Intron 1 | 175-231 bp |
| Exon 2 | 232-459 bp |
| Intron 2 | 460-525 bp |
| Exon 3 | 526-743 bp |
| Intron 3 | 744-798 bp |
| Exon 4 | 799-800 bp |
| Intron 4 | 801-858 bp |
| Exon 5 | 859-879 bp |
| Intron 5 | 880-935 bp |
| Exon 6 | 936-1082 bp |
| Intron 6 | 1083-1142 bp |
| Exon 7 | 1143-1447 bp |
| Intron 7 | 1448-1506 bp |
| Exon 8 | 1507-1617 bp |

Features (in base pairs) of SEQ ID NO: 9:

| | |
|---|---|
| Signal Peptide | 1-57 bp |
| Cellulose Binding Module 1 (CBM 1) | 58-168 bp |
| Linker | 169-174, 232-315 bp |
| Xylanase catalytic site | 316-459, 526-743, 799-800, 859-879, 936-1082, 1143-1447, 1507-1614 bp |
| Stop codon | 1615-1617 bp |

Protein Sequence of *Trametes versicolor* Strain NN055586 protein (SEQ ID NO: 10):

```
  1 MQLSTTFTLL AAIIPFALGQ AAEWGQCGGI GWTGATTCVA GTTCTVMNAY YSQCLPGSAA
 61 PAPTTTPTSP SSPATPPSAP APTGSGLNKL AKAAGKLYLG TATDNSELTD AAYTAILDDN
121 SQFGQITPAN SMKWDATEPT RGTFTFSGGD QIANLAKTNG MLLRGHNCVW YNQLPSWVAN
181 GQFTAADLTT VIQTHCSTLV SHYKGQVYSW DVVNEPFNDD GTWRSDVFYN TLGTSYVPIA
241 LKAARAADPS AKLYINDYNI EQTGAKATAM LNLVKQLIAD GVPIDGVGFQ CHFIVGEVPG
301 SFQTVLEQFT ALGLEVAITE LDIRTTTPAS QSALAQQEKD YQSVIQACMN VKGCVGATLW
361 DFTDKYSWVP STFSGQGAAC PWDQNLVKKP AYTGIVNALS A
```

Features of SEQ ID NO: 10 (amino acid positions):

| | |
|---|---|
| Signal Peptide | 1-19 |
| Cellulose Binding Module 1 (CBM 1) | 20-56 |
| Linker | 57-86 |
| Xylanase catalytic site | 87-401 |

Signal Peptide Sequence of SEQ ID NO: 10:

MQLSTTFTLLAAIIPFALG

*Trametes versicolor* Strain NN055586 Genomic Nucleotide Sequence (SEQ ID NO: 11):

```
  1 ATGAAGGGCC TCGCCGCACT CGTCGCACTC GCCACCATCG TCGCCGTCCC GGCCAACGCC GTCGCGGTCT GGGGCCAATG
 81 TGAGCATCCC TCACCCGGAC TTATACCTCT GGAATAGTAA CACTGACATG CGTTTGCAGG CGGAGTACGC ACCTTTGCCC
161 GCTGCGCTCG TCCTGTCTAC GCTTGACACT GACCTCTCTG TCAGGGTATC GGCTTCAGTG GATCGACCAC ATGTGATGCC
241 GGCACCACAT GCATCGTGCT CAACTCCTAC TACTCGCAGT GCCAGCCGGG TGCGAGCGCG CCCGCGCCCA CGACATCCGC
321 CCCCCAGCCG CCCCCGACCA CACCGGCTGG TGGCTCGCCC GCGCCCGCGG CGACCGGACT CAACGCTGCG TTCAAGAAGC
401 ACGGCAAGAA GTTCTGGGGC ACCGCGACGG ACTCAAACCG CTTCAGCAAC CCGACGGACT CCGCGGTCAC CGTCCGCGAG
481 TTCGCCAGG TCACGCCTGA GAACTCCATG AAGTGGGATG CGGTGAGTGC CTACTGGGCG CGTCGGCGTC GAGTGAGCAT
561 GTGCTTATGA TTATTTTCGT CGTAGACTGA GCGTGCGTAT TTAGTGAGGC TTCGGATGGT CCTCCCAGGA AACTGACAGC
641 ATGTTGCAGC TTCCCGCAAC CAGTTCTCGT TCAGCGGCTC TGATGCGCTG GTCAACTTCG CTACGACGAA TGGCCTGCTC
```

```
 721 GTCCGCGCTC ACACCCTCGG TAAGCATGTT CTCGTTGTCT CATCTCTGAA GTGGCGACTA ACTGTTCTTG GGGCGCAGTC

801 TGGCATTCGC AACTGCCGTC CTGGGTCTCT GCGATCAACG ACCGCGCGAC GCTCACGTCC GTGATCCAGA ACCACATCGC

881 GAACGTCGCA GGCCGGTACA AGGGCAAGGT GTACTCCTGG GACGTCGTGA ACGAGATCTT CAACGAGGAC GGCACGTTCC

961 GCTCGTCGGT GTTTTCAAAC GTCCTCGGCC AGGACTTCGT CACGATCGCG TTCCAGGCGG CACGGGCGGC GGACCCGAAC

1041 GCGAAGCTCT ACATCAACGA CTACAAGTGT GTCTCGCGGG TTGGCTTGGT GTGCCTTTGC TGATGCGTTT GTGTATGCAG

1121 CCTCGACACC GTGAACCCAA AGCTCAACGG TGTTGTCAAC CTTGTCAAGA AGATCAACGG CGGCGGCACC AAGCTGATCG

1201 ACGGTATCGG TACTCAGGCC CACCTTTCGG TAAGTGTATC AGGACTATTT AGCAGACTGA CGTGCTGACG CTAGAGCTCG

1281 GATAGGCTGG CGGCGCTGGC GGATTCCAGG CTGCGCTCAC GCAGCTGGCT ACCGCCGGCA CGGAGATCGC TATCACGGAG

1361 CTCGACATTG CGGGTGCCGT AAGTATCCGT TACAATGATT TCGCGCTGCT CCTTATTTAT GTCGCATTCA GGCCCCCAAT

1441 GACTACTCGA CGCTGGTCAA GGCGTGTCTC GCGGTGGAGA GCTGCGTGTC CATCACAAGC TGGGGAGTCC GCGATCCCGT

1521 AAGCAATATA TCTTCCTTGT TGACGGTGAT GAGACGTTCT CACCATGTGC ATGCTTTTAT CAGGACTCCT GGAGGGCGTC

1601 CACCAACCCC CTCTTGTTCG ACGCGAACTT CAACCCGAAG CCCGCATACA CTGCGGTTAT GCAGGCCCTG GCTTGA
```

Exons/Introns (in base pairs) of SEQ ID NO: 11:

| | |
|---|---|
| Exon 1 | 1-79 bp |
| Intron 1 | 80-139 bp |
| Exon 2 | 140-174 bp |
| Intron 2 | 175-204 bp |
| Exon 3 | 205-522 bp |
| Intron 3 | 523-585 bp |
| Exon 4 | 586-592 bp |
| Intron 4 | 593-649 bp |
| Exon 5 | 650-739 bp |
| Intron 5 | 740-798 bp |
| Exon 6 | 799-1066 bp |
| Intron 6 | 1067-1120 bp |
| Exon 7 | 1121-1229 bp |
| Intron 7 | 1230-1285 bp |
| Exon 8 | 1286-1378 bp |
| Intron 8 | 1379-1431 bp |
| Exon 9 | 1432-1518 bp |
| Intron 9 | 1519-1583 bp |
| Exon 10 | 1584-1676 bp |

Features (in base pairs) of SEQ ID NO: 11:

| | |
|---|---|
| Signal Peptide | 1-66 bp |
| Cellulose Binding Module 1 (CBM 1) | 67-79, 140-174, 205-288 bp |
| Linker | 289-378 bp |
| Xylanase catalytic site | 379-522, 586-592, 650-739, 799-1066, 1121-1229, 1286-1378, 1432-1518, 1584-1673 bp |
| Stop codon | 1674-1676 bp |

Protein Sequence of *Trametes versicolor* Strain NN055586 protein (SEQ ID NO: 12):

```
  1 MKGLAALVAL ATIVAVPANA VAVWGQCGVR TFARCARPGI GFSGSTTCDA GTTCIVLNSY

61 YSQCQPGASA PAPTTSAPQP PPTTPAGGSP APAATGLNAA FKKHGKKFWG TATDSNRFSN

121 PTDSAVTVRE FGQVTPENSM KWDATEPSRN QFSFSGSDAL VNFATTNGLL VRAHTLVWHS

181 QLPSWVSAIN DRATLTSVIQ NHIANVAGRY KGKVYSWDVV NEIFNEDGTF RSSVFSNVLG

241 QDFVTIAFQA ARAADPNAKL YINDYNLDTV NPKLNGVVNL VKKINGGGTK LIDGIGTQAH

301 LSAGGAGGFQ AALTQLATAG TEIAITELDI AGAAPNDYST LVKACLAVES CVSITSWGVR

361 DPDSWRASTN PLLFDANFNP KPAYTAVMQA LA
```

Features of SEQ ID NO: 12 (amino acid positions):

| | |
|---|---|
| Signal Peptide | 1-22 |
| Cellulose Binding Module 1 (CBM 1) | 23-66 |
| Linker | 67-96 |
| Xylanase catalytic site | 97-392 |

Signal Peptide Sequence of SEQ ID NO: 12:

MKGLAALVALATIVAVPANAVA

DEFINITIONS

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer. In one aspect, the polypeptides of the present invention have at least 20%, e.g., at least 40%, at least 50%, at least 60%, at least 70%, at least 80%, at least 90%, at least 95%, or at least 100% of the xylanase activity of the mature polypeptide of SEQ ID NO: 2, SEQ ID NO: 4, SEQ ID NO: 6, SEQ ID NO: 8, SEQ ID NO: 10, or SEQ ID NO: 12.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 μmole of glucuronic or 4-O-methyl-glucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No. 1 filter paper, microcrystalline cellulose, bacterial cellulose, algal cellulose, cotton, pretreated lignocellulose, etc. The most common total cellulolytic activity assay is the filter paper assay using Whatman No. 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide main; wherein the fragment has xylanase activity. In one aspect, a fragment contains at least 20 amino acid residues, e.g., at least 30 to 351 amino acid residues or at least 50 to 340, 80 to 310, 100 to 290, 150 to 270, or 200 to 250, or any number in between, amino acid residues of SEQ ID NO: 2. In another aspect, a fragment contains at least 20 amino acid residues, e.g., at least 30 to 350 amino acid residues or at least 50 to 340, 80 to 320, 100 to 300, 150 to 270, or 200 to 250, or any number in between, amino acid residues of SEQ ID NO: 4. In another aspect, a fragment contains at least 20 amino acid residues, e.g., at least 30 to 341 amino acid residues or at least 50 to 330, 80 to 310, 100 to 290, 150 to 270, or 200 to 250, or any number in between, amino acid residues of SEQ ID NO: 6. In another aspect, a fragment contains at least 20 amino acid residues, e.g., at least 30 to 394 amino acid residues or at least 50 to 380, 80 to 360, 100 to 340, 150 to 300, or 200 to 250, or any number in between, amino acid residues of SEQ ID NO: 8. In another aspect, a fragment contains at least 20 amino acid residues, e.g., at least 30 to 400 amino acid residues or at least 50 to 390, 80 to 360, 100 to 340, 150 to 300, or 200 to 250, or any number in between, amino acid residues of SEQ ID NO: 10. In another aspect, a fragment contains at least 20 amino acid residues, e.g., at least 30 to 391 amino acid residues or at least 50 to 380, 80 to 360, 100 to 340, 150 to 300, or 200 to 250, or any number in between, amino acid residues of SEQ ID NO: 12.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 19 to 352 of SEQ ID NO: 2 based on the SignalP program (Nielsen et al., 1997, *Protein Engineering* 10:1-6) that predicts amino acids 1 to 18 of SEQ ID NO: 2 are a signal peptide. In another aspect, the mature polypeptide is amino acids 1 to 352 of SEQ ID NO: 2. In another aspect, the mature polypeptide is amino acids 21 to 351 of SEQ ID NO: 4 based on the SignalP program that predicts amino acids 1 to 20 of SEQ ID NO: 4 are a signal peptide. In another aspect, the mature polypeptide is amino acids 1 to 351 of SEQ ID NO: 4. In another aspect, the mature polypeptide is amino acids 24 to 342 of SEQ ID NO: 6 based on the SignalP program that predicts amino acids 1 to 23 of SEQ ID NO: 6 are a signal peptide. In another aspect, the mature polypeptide is amino acids 1 to 342 of SEQ ID NO: 6. In another aspect, the mature polypeptide is amino acids 20 to 395 of SEQ ID NO: 8 based on the SignalP program that predicts amino acids 1 to 19 of SEQ ID NO: 8 are a signal peptide. In another aspect, the mature polypeptide is amino acids 1 to 395 of SEQ ID NO: 8. In another aspect, the mature polypeptide is amino acids 20 to 401 of SEQ ID NO: 10 based on the SignalP program that predicts amino acids 1 to 19 of SEQ ID NO: 10 are a signal peptide. In another aspect, the mature polypeptide is amino acids 1 to 401 of SEQ ID NO: 10. In another aspect, the mature polypeptide is amino acids 23 to 392 of SEQ ID NO: 12 based on the SignalP program that predicts amino acids 1 to 22 of SEQ ID NO: 12 are a signal peptide. In another aspect, the mature polypeptide is amino acids 1 to 392 of SEQ ID NO: 12. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having xylanase activity. In one aspect, the mature polypeptide coding sequence is nucleotides 55 to 1515 of SEQ ID NO: 1 or the cDNA sequence thereof based on the SignalP program (Nielsen et al., 1997, supra) that predicts nucleotides 1 to 54 of SEQ ID NO: 1 encode a signal peptide. In another aspect, the mature polypeptide coding sequence is nucleotides 1 to 1515 of SEQ ID NO: 1 or the cDNA sequence thereof. In another aspect, the mature polypeptide coding sequence is nucleotides 61 to 1461 of SEQ ID NO: 3 or the cDNA sequence thereof based on the SignalP program that predicts nucleotides 1 to 60 of SEQ ID NO: 3 encode a signal peptide. In another aspect, the mature polypeptide coding sequence is nucleotides 1 to 1461 of SEQ ID NO: 3 or the cDNA sequence thereof. In another aspect, the mature polypeptide coding sequence is nucleotides 70 to 1400 of SEQ ID NO: 5 or the cDNA sequence thereof based on the SignalP program that predicts nucleotides 1 to 69 of SEQ ID NO: 5 encode a signal peptide. In another aspect, the mature polypeptide coding sequence is nucleotides 1 to 1400 of SEQ ID NO: 5 or the cDNA sequence thereof. In another aspect, the mature polypeptide coding sequence is nucleotides 58 to 1665 of SEQ ID NO: 7 or the cDNA sequence thereof based on the SignalP program that predicts nucleotides 1 to 57 of SEQ ID NO: 7 encode a signal peptide. In another aspect, the mature polypeptide coding sequence is nucleotides 1 to 1665 of SEQ ID NO: 7 or the cDNA sequence thereof. In another aspect, the mature polypeptide coding sequence is nucleotides 58 to 1614 of SEQ ID NO: 9 or the cDNA sequence thereof based on the SignalP program that predicts nucleotides 1 to 57 of SEQ ID NO: 9 encode a signal peptide. In another aspect, the mature polypeptide coding sequence is nucleotides 1 to 1614 of SEQ ID NO: 9 or the cDNA sequence thereof. In another aspect, the mature polypeptide coding sequence is nucleotides 67 to 1673 of SEQ ID NO: 11 or the cDNA sequence thereof based on the SignalP program that predicts nucleotides 1 to 66 of SEQ ID NO: 11 encode a signal peptide. In another aspect, the mature polypeptide coding sequence is nucleotides 1 to 1673 of SEQ ID NO: 11 or the cDNA sequence thereof.

Catalytic domain: The term "catalytic domain" means the portion of an enzyme containing the catalytic machinery of the enzyme.

Cellulose binding domain: The term "cellulose binding domain" means the portion of an enzyme that mediates binding of the enzyme to amorphous regions of a cellulose substrate. The cellulose binding domain (CBD) is found either at the N-terminal or at the C-terminal extremity of an enzyme. A CBD is also referred to as a cellulose binding module or CBM. In one embodiment the CBM is amino acids 20 to 56 of SEQ ID NO: 8. In one embodiment the CBM is amino acids 20 to 56 of SEQ ID NO: 10. In one embodiment the CBM is amino acids 23 to 66 of SEQ ID NO: 12. The CBM is separated from the catalytic domain by a linker sequence. The linker is in one embodiment amino acids 57 to 81 of SEQ ID NO: 8. The linker is in one embodiment amino acids 57 to 86 of SEQ ID NO: 10. The linker is in one embodiment amino acids 67 to 96 of SEQ ID NO: 12.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having xylanase activity. In one aspect, a subsequence contains at least 800 nucleotides, e.g., at least 1000 nucleotides or at least 1100 nucleotides of SEQ ID NO: 1. In another aspect, a subsequence contains at least 800 nucleotides, e.g., at least 1000 nucleotides or at least 1100 nucleotides of SEQ ID NO: 3. In another aspect, a subsequence contains at least 800 nucleotides, e.g., at least 1000 nucleotides or at least 1100 nucleotides of SEQ ID NO: 5. In another aspect, a subsequence contains at least 800 nucleotides, e.g., at least 1000 nucleotides or at least 1100 nucleotides of SEQ ID NO: 7. In another aspect, a subsequence contains at least 800 nucleotides, e.g., at least 1000 nucleotides or at least 1100 nucleotides of SEQ ID NO: 9. In another aspect, a subsequence contains at least 800 nucleotides, e.g., at least 1000 nucleotides or at least 1100 nucleotides of SEQ ID NO: 11.

Variant: The term "variant" means a polypeptide having xylanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, Biochemical Journal 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

DETAILED DESCRIPTION OF THE INVENTION

Polypeptides Having Xylanase Activity

In an embodiment, the present invention relates to isolated polypeptides having a sequence identity to the mature polypeptide of SEQ ID NO: 2 of at least 67%, e.g., at least 68%, at least 69%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have xylanase activity. In an embodiment, the present invention relates to isolated polypeptides having a sequence identity to the mature polypeptide of SEQ ID NO: 4 of at least 61%, e.g., at least 62%, at least 63%, at least 65%, at least 67%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have xylanase activity. In an embodiment, the present invention relates to isolated polypeptides having a sequence identity to the mature polypeptide of SEQ ID NO: 6 of at least 61%, e.g., at least 62%, at least 63%, at least 65%, at least 67%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have xylanase activity. In an embodiment, the present invention relates to isolated polypeptides having a sequence identity to the mature polypeptide of SEQ ID NO: 8 of at least 90%, e.g., at least 91%, at least 92%, at least 93%, at least 94%, at least 95%, at least 96%, at least 97%, at least 98%, at least 99%, or 100%, which have xylanase activity. In an embodiment, the present invention relates to isolated polypeptides having a sequence identity to the mature polypeptide of SEQ ID NO: 10 of at least 79%, e.g., at least 80%, at least 83%, at least 85%, at least 87%, at least 88%, at least 89%, at least 90%, at least 91%, at least 92%, at least 93%, at least 94%, at least 95%, at least 96%, at least 97%, at least 98%, at least 99%, or 100%, which have xylanase activity. In an embodiment, the present invention relates to isolated polypeptides having a sequence identity to the mature polypeptide of SEQ ID NO: 12 of at least 92%, e.g., at least 93%, at least 94%, at least 95%, at least 96%, at least 97%, at least 98%, at least 99%, or 100%, which have xylanase activity. In one aspect, the polypeptides differ by no more than 10 amino acids, e.g., 1, 2, 3, 4, 5, 6, 7, 8, or 9, from the mature polypeptide of SEQ ID NO: 2, SEQ ID NO: 4, SEQ ID NO: 6, SEQ ID NO: 8, SEQ ID NO: 10, or SEQ ID NO: 12.

A polypeptide of the present invention preferably comprises or consists of the amino acid sequence of SEQ ID NO: 2, SEQ ID NO: 4, SEQ ID NO: 6, SEQ ID NO: 8, SEQ ID NO: 10, or SEQ ID NO: 12 or an allelic variant thereof; or is a fragment thereof having xylanase activity. In another aspect, the polypeptide comprises or consists of the mature polypeptide of SEQ ID NO: 2, SEQ ID NO: 4, SEQ ID NO: 6, SEQ ID NO: 8, SEQ ID NO: 10, or SEQ ID NO: 12. In another aspect, the polypeptide comprises or consists of amino acids 19 to 352 of SEQ ID NO: 2, amino acids 21 to 351 of SEQ ID NO: 4, amino acids 24 to 342 of SEQ ID NO: 6, amino acids 20 to 395 of SEQ ID NO: 8, amino acids 20 to 401 of SEQ ID NO: 10, or amino acids 23 to 392 of SEQ ID NO: 12.

In another embodiment, the present invention relates to an isolated polypeptide having xylanase activity encoded by a polynucleotide that hybridizes under very low stringency conditions, or low stringency conditions, or medium stringency conditions, or medium-high stringency conditions, or high stringency conditions, or very high stringency conditions with (i) the mature polypeptide coding sequence of SEQ ID NO: 1, SEQ ID NO: 3, SEQ ID NO: 5, SEQ ID NO: 7, SEQ ID NO: 9, or SEQ ID NO: 11, (ii) the cDNA sequence thereof, or (iii) the full-length complement of (i) or (ii) (Sambrook et al., 1989, *Molecular Cloning, A Laboratory Manual,* 2d edition, Cold Spring Harbor, N.Y.).

The polynucleotide of SEQ ID NO: 1, SEQ ID NO: 3, SEQ ID NO: 5, SEQ ID NO: 7, SEQ ID NO: 9, or SEQ ID NO: 11, or a subsequence thereof, as well as the polypeptide of SEQ ID NO: 2, SEQ ID NO: 4, SEQ ID NO: 6, SEQ ID NO: 8, SEQ ID NO: 10, or SEQ ID NO: 12, or a fragment thereof, may be used to design nucleic acid probes to identify and clone DNA encoding polypeptides having xylanase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having xylanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, SEQ ID NO: 5, SEQ ID NO: 7, SEQ ID NO: 9, or SEQ ID NO: 11 or a subsequence thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 3, SEQ ID NO: 5, SEQ ID NO: 7, SEQ ID NO: 9, or SEQ ID NO: 11; (ii) the mature polypeptide coding sequence of SEQ ID NO: 1, SEQ ID NO: 3, SEQ ID NO: 5, SEQ ID NO: 7, SEQ ID NO: 9, or SEQ ID NO: 11; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2, SEQ ID NO: 4, SEQ ID NO: 6, SEQ ID NO: 8, SEQ ID NO: 10, or SEQ ID NO: 12; the mature polypeptide thereof; or a fragment thereof. In another aspect, the nucleic acid probe is SEQ ID NO: 1, SEQ ID NO: 3, SEQ ID NO: 5, SEQ ID NO: 7, SEQ ID NO: 9, or SEQ ID NO: 11; or the cDNA sequence thereof. In another aspect, the nucleic acid probe is the polynucleotide contained in *Trametes versicolor* Strain NN055586, wherein the polynucleotide encodes a polypeptide having xylanase activity.

In another embodiment, the present invention relates to an isolated polypeptide having xylanase activity encoded by a polynucleotide having a sequence identity to the mature polypeptide coding sequence of SEQ ID NO: 1, SEQ ID NO: 3, SEQ ID NO: 5, SEQ ID NO: 7, SEQ ID NO: 9, or SEQ ID NO: 11, or the cDNA sequence thereof, of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, SEQ ID NO: 4, SEQ ID NO: 6, SEQ ID NO: 8, SEQ ID NO: 10, or SEQ ID NO: 12 comprising a substitution, deletion, and/or insertion at one or more (e.g., several) positions. In an embodiment, the number of amino acid substitutions, deletions and/or insertions introduced into the mature polypeptide of SEQ ID NO: 2, SEQ ID NO: 4, SEQ ID NO: 6, SEQ ID NO: 8, SEQ ID NO: 10, or SEQ ID NO: 12 is not more than 10, e.g., 1, 2, 3, 4, 5, 6, 7, 8 or 9. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for xylanase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having [Enzyme] Activity

A polypeptide having xylanase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a *Trametes* polypeptide.

In another aspect, the polypeptide is a *Trametes versicolor* polypeptide, e.g., a polypeptide obtained from *Trametes versicolor* Strain NN055586, or in another aspect the polypeptide is a polypeptide from a species related to *Trametes versicolor*, for example from another *Trametes* species.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

The present invention also relates to isolated polypeptides comprising a catalytic domain selected from the group consisting of:

(a) a catalytic domain having at least 60% sequence identity to the catalytic domain of SEQ ID NO: 2 (for example, amino acids 19 to 352 of SEQ ID NO: 2), a catalytic domain having at least 60% sequence identity to the catalytic domain of SEQ ID NO: 4 (for example, amino acids 21 to 351 of SEQ ID NO: 4), a catalytic domain having at least 60% sequence identity to the catalytic domain of SEQ ID NO: 6 (for example, amino acids 24 to 342 of SEQ ID NO: 6), a catalytic domain having at least 60% sequence identity to the catalytic domain of SEQ ID NO: 8 (for example, amino acids 82 to 395 of SEQ ID NO: 8), a catalytic domain having at least 60% sequence identity to the catalytic domain of SEQ ID NO: 10 (for example, amino acids 87 to 401 of SEQ ID NO: 10), or a catalytic domain having at least 60% sequence identity to the catalytic domain of SEQ ID NO: 12 (for example, amino acids 97 to 392 of SEQ ID NO: 12);

(b) a catalytic domain encoded by a polynucleotide having at least 60% sequence identity to the catalytic domain coding sequence of SEQ ID NO: 1 (for example, nucleotides 55-1515 of SEQ ID NO: 1), a catalytic domain encoded by a polynucleotide having at least 60% sequence identity to the catalytic domain coding sequence of SEQ ID NO: 3 (for example, nucleotides 60-249, 307-524, 649-665, 721-867, 930-1237, 1295-1351, and 1405-1461 of SEQ ID NO: 3), a catalytic domain encoded by a polynucleotide having at least 60% sequence identity to the catalytic domain coding sequence of SEQ ID NO: 5 (for example, nucleotides 79-273, 325-430, 472-598, 718-734, 789-935, 990-1297, and 1353-1400 of SEQ ID NO: 5), a catalytic domain encoded by a polynucleotide having at least 60% sequence identity to the catalytic domain coding sequence of SEQ ID NO: 7 (for example, nucleotides 310-453, 511-728, 786-787, 845-865, 923-1069, 1137-1441, 1503-1559, and 1618-1665 of SEQ ID NO: 7), a catalytic domain encoded by a polynucleotide having at least 60% sequence identity to the catalytic domain coding sequence of SEQ ID NO: 9 (for example, nucleotides 316-459, 526-743, 799-800, 859-879, 936-1082, 1143-1447, and 1507-1614 of SEQ ID NO: 9), or a catalytic domain encoded by a polynucleotide having at least 60% sequence identity to the catalytic domain coding sequence of SEQ ID NO: 11 (for example, nucleotides 379-522, 586-592, 650-739, 799-1066, 1121-1229, 1286-1378, 1432-1518, and 1584-1673 of SEQ ID NO: 11);

(c) a variant of a catalytic domain comprising a substitution, deletion, and/or insertion of one or more (several) amino acids of the catalytic domain of SEQ ID NO: 2, SEQ ID NO: 4, SEQ ID NO: 6, SEQ ID NO: 8, SEQ ID NO: 10, or SEQ ID NO: 12; and (d) a fragment of a catalytic domain of (a), (b), or (c), which has xylanase activity.

The catalytic domain preferably has a degree of sequence identity to the catalytic domain of SEQ ID NO: 2, SEQ ID NO: 4, SEQ ID NO: 6, SEQ ID NO: 8, SEQ ID NO: 10, or SEQ ID NO: 12 of at least 60%, e.g. at least 70%, at least 75%, at least 80%, at least 85%, at least 90%, at least 91%, at least 92%, at least 95%, at least 96%, at least 97%, at least 98%, at least 99%, or 100%. In an aspect, the catalytic domain comprises an amino acid sequence that differs by ten amino acids, e.g., by five amino acids, by four amino acids, by three amino acids, by two amino acids, and by one amino acid from the catalytic domain of SEQ ID NO: 2, SEQ ID NO: 4, SEQ ID NO: 6, SEQ ID NO: 8, SEQ ID NO: 10, or SEQ ID NO: 12.

The catalytic domain preferably comprises or consists of the catalytic domain of SEQ ID NO: 2 or an allelic variant thereof; or is a fragment thereof having xylanase activity. In another preferred aspect, the catalytic domain comprises or consists of amino acids 19 to 352 of SEQ ID NO: 2.

The catalytic domain preferably comprises or consists of the catalytic domain of SEQ ID NO: 4 or an allelic variant thereof; or is a fragment thereof having xylanase activity. In another preferred aspect, the catalytic domain comprises or consists of amino acids 21 to 351 of SEQ ID NO: 4.

The catalytic domain preferably comprises or consists of the catalytic domain of SEQ ID NO: 6 or an allelic variant thereof; or is a fragment thereof having xylanase activity. In another preferred aspect, the catalytic domain comprises or consists of amino acids 24 to 342 of SEQ ID NO: 6.

The catalytic domain preferably comprises or consists of the catalytic domain of SEQ ID NO: 8 or an allelic variant thereof; or is a fragment thereof having xylanase activity. In another preferred aspect, the catalytic domain comprises or consists of amino acids 82 to 395 of SEQ ID NO: 8.

The catalytic domain preferably comprises or consists of the catalytic domain of SEQ ID NO: 10 or an allelic variant thereof; or is a fragment thereof having xylanase activity. In another preferred aspect, the catalytic domain comprises or consists of amino acids 87 to 401 of SEQ ID NO: 10.

The catalytic domain preferably comprises or consists of the catalytic domain of SEQ ID NO: 12 or an allelic variant thereof; or is a fragment thereof having xylanase activity. In another preferred aspect, the catalytic domain comprises or consists of amino acids 97 to 392 of SEQ ID NO: 12.

In an embodiment, the catalytic domain may be encoded by a polynucleotide that hybridizes under very low stringency conditions, or low stringency conditions, or medium stringency conditions, or medium-high stringency conditions, or high stringency conditions, or very high stringency conditions (as defined above) with (i) the catalytic domain coding sequence of SEQ ID NO: 1, SEQ ID NO: 3, SEQ ID NO: 5, SEQ ID NO: 7, SEQ ID NO: 9, or SEQ ID NO: 11, (ii) the cDNA sequence contained in the catalytic domain coding sequence of SEQ ID NO: 1, SEQ ID NO: 3, SEQ ID NO: 5, SEQ ID NO: 7, SEQ ID NO: 9, or SEQ ID NO: 11, or (iii) the full-length complementary strand of (i) or (ii) (J. Sambrook et al., 1989, supra).

The catalytic domain may be encoded by a polynucleotide having a degree of sequence identity to the catalytic domain coding sequence of SEQ ID NO: 1, SEQ ID NO: 3, SEQ ID NO: 5, SEQ ID NO: 7, SEQ ID NO: 9, or SEQ ID NO: 11 of at least 60%, e.g. at least 70%, at least 75%, at least 80%, at least 85%, at least 90%, at least 91%, at least 92%, at least 95%, at least 96%, at least 97%, at least 98%, at least 99%, or 100%, which encode a polypeptide having xylanase activity.

In one aspect, the polynucleotide encoding the catalytic domain comprises or consists of nucleotides 55 to 1515 of SEQ ID NO: 1 or the cDNA sequence thereof. In particular the polynucleotide encoding the catalytic domain comprises or consists of nucleotides 55-1515 of SEQ ID NO: 1.

In one aspect, the polynucleotide encoding the catalytic domain comprises or consists of nucleotides 61 to 1461 of SEQ ID NO: 3 or the cDNA sequence thereof. In particular the polynucleotide encoding the catalytic domain comprises or consists of nucleotides 61-249, 307-524, 649-665, 721-867, 930-1237, 1295-1351, and 1405-1461 of SEQ ID NO: 3.

In one aspect, the polynucleotide encoding the catalytic domain comprises or consists of nucleotides 79 to 1400 of SEQ ID NO: 5 or the cDNA sequence thereof. In particular the polynucleotide encoding the catalytic domain comprises or consists of nucleotides 79-273, 325-430, 472-598, 718-734, 789-935, 990-1297, and 1353-1400 of SEQ ID NO: 5.

In one aspect, the polynucleotide encoding the catalytic domain comprises or consists of nucleotides 310 to 1665 of SEQ ID NO: 7 or the cDNA sequence thereof. In particular the polynucleotide encoding the catalytic domain comprises or consists of nucleotides 310-453, 511-728, 786-787, 845-865, 923-1069, 1137-1441, 1503-1559, and 1618-1665 of SEQ ID NO: 7.

In one aspect, the polynucleotide encoding the catalytic domain comprises or consists of nucleotides 316 to 1614 of SEQ ID NO: 9 or the cDNA sequence thereof. In particular the polynucleotide encoding the catalytic domain comprises or consists of nucleotides 316-459, 526-743, 799-800, 859-879, 936-1082, 1143-1447, and 1507-1614 of SEQ ID NO: 9.

In one aspect, the polynucleotide encoding the catalytic domain comprises or consists of nucleotides 379 to 1673 of SEQ ID NO: 11 or the cDNA sequence thereof. In particular the polynucleotide encoding the catalytic domain comprises or consists of nucleotides 379-522, 586-592, 650-739, 799-1066, 1121-1229, 1286-1378, 1432-1518, and 1584-1673 of SEQ ID NO: 11.

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Trametes*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 3, SEQ ID NO: 5, SEQ ID NO: 7, SEQ ID NO: 9, or SEQ ID NO: 11, or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus neutral* alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (*Praha*) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is a *Trametes* cell. In a more preferred aspect, the cell is a *Trametes versicolor* cell. In a most preferred aspect, the cell is *Trametes versicolor* Strain NN055586.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification,* Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium,* temperate grass, such as *Agrostis,* and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Compositions

The present invention also relates to compositions comprising a polypeptide of the present invention. Preferably, the compositions are enriched in such a polypeptide. The term "enriched" indicates that the xylanase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as one or more (e.g., several) enzymes selected from the group consisting of a cellulase, a hemicellulase, GH61 polypeptide, an expansin, an esterase, a laccase, a ligninolytic enzyme, a pectinase, a peroxidase, a protease, and a swollenin.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to the following processes for using the polypeptides having xylanase activity, or compositions thereof.

The present invention also relates to processes for degrading a cellulosic material or xylan-containing material, comprising: treating the cellulosic material or xylan-containing material with an enzyme composition in the presence of a polypeptide having xylanase activity of the present invention. In one aspect, the processes further comprise recovering the degraded or converted cellulosic material or xylan-containing material. Soluble products of degradation or conversion of the cellulosic material or xylan-containing material can be separated from insoluble cellulosic material or xylan-containing material using a method known in the art such as, for example, centrifugation, filtration, or gravity settling.

The present invention also relates to processes of producing a fermentation product, comprising: (a) saccharifying a cellulosic material or xylan-containing material with an enzyme composition in the presence of a polypeptide having xylanase activity of the present invention; (b) fermenting the saccharified cellulosic material or xylan-containing material with one or more (e.g., several) fermenting microorganisms to produce the fermentation product; and (c) recovering the fermentation product from the fermentation.

The present invention also relates to processes of fermenting a cellulosic material or xylan-containing material, comprising: fermenting the cellulosic material or xylan-containing material with one or more (e.g., several) fermenting microorganisms, wherein the cellulosic material or xylan-containing material is saccharified with an enzyme composition in the presence of a polypeptide having xylanase activity of the present invention. In one aspect, the fermenting of the cellulosic material or xylan-containing material produces a fermentation product. In another aspect, the processes further comprise recovering the fermentation product from the fermentation.

The processes of the present invention can be used to saccharify the cellulosic material or xylan-containing material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material or xylan-containing material typically involves pretreatment, enzymatic hydrolysis (saccharification), and fermentation.

The processing of the cellulosic material or xylan-containing material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material or xylan-containing material to fermentable sugars, e.g., glucose, cellobiose, and pentose monomers, and then ferment the fermentable sugars to ethanol. In SSF, the enzymatic hydrolysis of the cellulosic material or xylan-containing material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material or xylan-containing material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum*. Technology 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material or xylan-containing material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material or xylan-containing material can also be subjected to particle size reduction, sieving, presoaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material or xylan-containing material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material or xylan-containing material is heated to disrupt the plant cell wall components, including lignin, hemicellulose, and cellulose to make the cellulose and other fractions, e.g., hemicellulose, accessible to enzymes. The cellulosic material or xylan-containing material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material or xylan-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material or xylan-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005,

*Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material or xylan-containing material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material or xylan-containing material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material or xylan-containing material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material or xylan-containing material is present during pretreatment in amounts preferably between 10-80 wt %, e.g., 20-70 wt % or 30-60 wt %, such as around 40 wt %. The pretreated cellulosic material or xylan-containing material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material or xylan-containing material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material or xylan-containing material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material or xylan-containing material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N.J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material or xylan-containing material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a polypeptide having xylanase activity of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material or xylan-containing material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material or xylan-containing material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another aspect, the cellulase is preferably one or more (e.g., several) enzymes selected from the group consisting of an endoglucanase, a cellobiohydrolase, and a beta-glucosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin In the processes of the present invention, the enzyme(s) can be added prior to or during fermentation, e.g., during saccharification or during or after propagation of the fermenting microorganism(s).

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a crude fermentation broth with or without cells removed, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and polypeptides having xylanase activity depend on several factors including, but not limited to, the mixture of component cellulolytic enzymes, the cellulosic material or xylan-containing material, the concentration of cellulosic material or xylan-containing material, the pretreatment(s) of the cellulosic material or xylan-containing material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material or xylan-containing material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material or xylan-containing material.

In another aspect, an effective amount of a polypeptide having xylanase activity to the cellulosic material or xylan-containing material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material or xylan-containing material.

In another aspect, an effective amount of a polypeptide having xylanase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material or xylan-containing material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a gram positive bacterial polypeptide such as a *Bacillus*, *Streptococcus*, *Streptomyces*, *Staphylococcus*, *Enterococcus*, *Lactobacillus*, *Lactococcus*, *Clostridium*, *Geobacillus*, *Caldicellulosiruptor*, *Acidothermus*, *Thermobifidia*, or *Oceanobacillus* polypeptide having enzyme activity, or a Gram negative bacterial polypeptide such as an *E. coli*, *Pseudomonas*, *Salmonella*, *Campylobacter*, *Helicobacter*, *Flavobacterium*, *Fusobacterium*, *Ilyobacter*, *Neisseria*, or *Ureaplasma* polypeptide having enzyme activity.

In one aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polypeptide having enzyme activity.

In another aspect, the polypeptide is a *Streptococcus equisimilis*, *Streptococcus pyogenes*, *Streptococcus uberis*, or *Streptococcus equi* subsp. *Zooepidemicus* polypeptide having enzyme activity.

In another aspect, the polypeptide is a *Streptomyces achromogenes*, *Streptomyces avermitilis*, *Streptomyces coelicolor*, *Streptomyces griseus*, or *Streptomyces lividans* polypeptide having enzyme activity.

The polypeptide having enzyme activity may also be a fungal polypeptide, and more preferably a yeast polypeptide such as a *Candida*, *Kluyveromyces*, *Pichia*, *Saccharomyces*, *Schizosaccharomyces*, or *Yarrowia* polypeptide having enzyme activity; or more preferably a filamentous fungal polypeptide such as an *Acremonium*, *Agaricus*, *Alternaria*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide having enzyme activity.

In one aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide having enzyme activity.

In another aspect, the polypeptide is an *Acremonium cellulolyticus*, *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia*

*microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride*, or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC™ CTec (Novozymes A/S), CELLIC™ CTec2 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM). ROHAMENT™ 7069 W (Röhm GmbH), FIBREZYME® LDI (Dyadic International, Inc.), FIBREZYME® LBR (Dyadic International, Inc.), or VISCOSTAR® 150 L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydralase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In the processes of the present invention, any GH61 polypeptide having cellulolytic enhancing activity can be used.

Examples of GH61 polypeptides having cellulolytic enhancing activity useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese sulfate.

In one aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material or xylan-containing material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of thebicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of thenitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material or xylan-containing material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, ord about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-6}$ to about 1 g, about $10^{-6}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC™ HTec (Novozymes A/S), CELLIC™ HTec2 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8×212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number Q0CJP9), *Humicola insolens* (WO 2010/014706), *Penicillium aurantiogriseum* (WO 2009/068565), *Talaromyces emersonii* (UniProt accession number Q8×211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material or xylan-containing material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material or xylan-containing material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material or xylan-containing material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis,* and *C. scehatae; Clostridium*, such as *C. acetobutylicum, C. thermocellum,* and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans,* and *K. fragilis; Schizosaccharomyces*, such as *S. pombe; Thermoanaerobacter*, such as *Thermoanaerobacter saccharolyticum*; and *Zymomonas*, such as *Zymomonas mobilis*.

In a preferred aspect, the yeast is *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacilus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or xylan-containing material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material or xylan-containing material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N.J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material or xylan-containing material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptide

The present invention also relates to an isolated polynucleotide encoding a signal peptide comprising or consisting of amino acids 1 to 18 of SEQ ID NO: 2, amino acids 1 to 20 of SEQ ID NO: 4, amino acids 1 to 23 of SEQ ID NO: 6, amino acids 1 to 19 of SEQ ID NO: 8, amino acids 1 to 19 of SEQ ID NO: 10, or amino acids 1 to 22 of SEQ ID NO: 12. The polynucleotide may further comprise a gene encoding a protein, which is operably linked to the signal peptide. The protein is preferably foreign to the signal peptide. In one aspect, the polynucleotide encoding the signal peptide is nucleotides 1 to 54 of SEQ ID NO: 1. In another aspect, the polynucleotide encoding the signal peptide is nucleotides 1 to 60 of SEQ ID NO: 3. In another aspect, the polynucleotide encoding the signal peptide is nucleotides 1 to 69 of SEQ ID NO: 5. In another aspect, the polynucleotide encoding the signal peptide is nucleotides 1 to 57 of SEQ ID NO: 7. In another aspect, the polynucleotide encoding the signal peptide is nucleotides 1 to 57 of SEQ ID NO: 9. In another aspect, the polynucleotide encoding the signal peptide is nucleotides 1 to 66 of SEQ ID NO: 11.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The gene may be obtained from any prokaryotic, eukaryotic, or other source.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A nucleic acid construct or expression vector comprising a polynucleotide encoding a polypeptide having xylanase activity, wherein the polynucleotide is operably linked to one or more heterologous control sequences that direct production of the polypeptide and wherein the polypeptide having xylanase activity is selected from the group consisting of:
   (a) a polypeptide having at least 90% sequence identity to the mature polypeptide of SEQ ID NO: 6;
   (b) a polypeptide encoded by a polynucleotide that hybridizes under very high stringency conditions with (i) the mature polypeptide coding sequence of SEQ ID NO: 5, (ii) the cDNA thereof, or (iii) the full-length complement of (i) or (ii), wherein very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.;
   (c) a polypeptide encoded by a polynucleotide having at least 90% sequence identity to the mature polypeptide coding sequence of SEQ ID NO: 5 or the cDNA thereof;
   (d) a fragment of the polypeptide of (a), (b), or (c) that has xylanase activity;
   (e) a polypeptide comprising amino acids 24 to 342 of SEQ ID NO: 6; and
   (f) a polypeptide encoded by a polynucleotide comprising nucleotides 70 to 1400 of SEQ ID NO: 5 or the cDNA thereof.

2. An isolated recombinant host cell comprising the nucleic acid construct or vector of claim 1.

3. A method of producing a polypeptide having xylanase activity, the method comprising:
   (a) cultivating the recombinant host cell of claim 2 under conditions conducive for production of the polypeptide; and
   (b) recovering the polypeptide.

4. A transgenic plant, plant part or plant cell transformed with a polynucleotide encoding a polypeptide having xylanase activity selected from the group consisting of:
   (a) a polypeptide having at least 90% sequence identity to the mature polypeptide of SEQ ID NO: 6;
   (b) a polypeptide encoded by a polynucleotide that hybridizes under very high stringency conditions with (i) the mature polypeptide coding sequence of SEQ ID NO: 5, (ii) the cDNA thereof, or (iii) the full-length complement of (i) or (ii), wherein very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.;
   (c) a polypeptide encoded by a polynucleotide having at least 90% sequence identity to the mature polypeptide coding sequence of SEQ ID NO: 5 or the cDNA thereof;
   (d) a fragment of the polypeptide of (a), (b), or (c) that has xylanase activity;
   (e) a polypeptide comprising amino acids 24 to 342 of SEQ ID NO: 6; and
   (f) a polypeptide encoded by a polynucleotide comprising nucleotides 70 to 1400 of SEQ ID NO: 5 or the cDNA thereof.

5. A method of producing a polypeptide having xylanase activity, the method comprising:
   (a) cultivating the transgenic plant or plant cell of claim 4 under conditions conducive for production of the polypeptide; and
   (b) recovering the polypeptide.

* * * * *